United States Patent
Bakan et al.

(10) Patent No.: US 10,953,021 B2
(45) Date of Patent: Mar. 23, 2021

(54) TOPICAL COMPOSITIONS OF FLUNISOLIDE AND METHODS OF TREATMENT

(71) Applicant: Lupin Limited, Mumbai (IN)

(72) Inventors: Douglas Anthony Bakan, San Diego, CA (US); Steven B. Newhard, Scottsdale, AZ (US); Nilendu Sen, Maharashtra (IN); Amol Subhash Mandhare, Maharashtra (IN); Tushar Deoram Jadhav, Maharashtra (IN); Mukesh Kumar, Maharashtra (IN)

(73) Assignee: Lupin Limited, Mumbai (IN)

( * ) Notice: Subject to any disclaimer, the term of this patent is extended or adjusted under 35 U.S.C. 154(b) by 0 days.

(21) Appl. No.: 14/213,530

(22) Filed: Mar. 14, 2014

(65) Prior Publication Data

US 2014/0274982 A1 Sep. 18, 2014

(30) Foreign Application Priority Data

Mar. 15, 2013 (IN) ................ 303KOL2013

(51) Int. Cl.
| | |
|---|---|
| *A61K 31/58* | (2006.01) |
| *A61K 47/10* | (2017.01) |
| *A61K 9/00* | (2006.01) |
| *A61K 9/06* | (2006.01) |
| *A61K 9/107* | (2006.01) |

(52) U.S. Cl.
CPC ............ *A61K 31/58* (2013.01); *A61K 9/0014* (2013.01); *A61K 9/06* (2013.01); *A61K 9/107* (2013.01); *A61K 9/1075* (2013.01); *A61K 47/10* (2013.01)

(58) Field of Classification Search
CPC ........ A61K 31/58; A61K 9/0014; A61K 9/06; A61K 9/107; A61K 47/10
See application file for complete search history.

(56) References Cited

U.S. PATENT DOCUMENTS

| | | | |
|---|---|---|---|
| 3,126,375 A | 3/1964 | Ringold et al. | |
| 4,427,670 A * | 1/1984 | Ofuchi | A61K 9/0014 514/114 |
| 4,933,168 A | 6/1990 | Jones et al. | |
| 2006/0045850 A1 | 3/2006 | Namburi et al. | |
| 2006/0246098 A1 | 11/2006 | Rao et al. | |
| 2007/0020299 A1* | 1/2007 | Pipkin et al. | 424/400 |
| 2011/0098267 A1* | 4/2011 | Babu et al. | 514/210.2 |
| 2011/0305643 A1* | 12/2011 | Gurge et al. | 424/45 |

FOREIGN PATENT DOCUMENTS

| | | |
|---|---|---|
| EP | 0173478 A1 | 5/1986 |
| EP | 0246652 A2 | 11/1987 |
| GB | 1525181 A | 9/1978 |
| WO | 94/12187 A1 | 6/1994 |
| WO | 97/38699 A2 | 10/1997 |
| WO | 2004/071469 A2 | 8/2004 |
| WO | WO-2006102004 A2 * | 9/2006 ............... A61K 8/06 |

OTHER PUBLICATIONS

Barclay-Nichols (Better crafting through chemistry: Dimethicone; 2009; http://swiftcraftymonkey.blogspot.com/2009/05/better-crafting-through-chemistry_10.html).*
Carbopol 980 Polymer (Lubrizol, 2009, https://web.archive.org/web/20090926221338/http://www.lubrizol.com/PersonalCare/Products/Carbopol/Carbopol980.html).*
Database WPI Section Ch, Week 200503, Thomson Scientific, London, GB, AN 2005-023283; XP002725813; Fujitsuka et al., "Nasal drop for treating allergic rhinitis, contains flunisolide and/or beclometasone, alchohol e.g. menthol, camphor, borneol or geraniol, and chlorobutanol, lidocaine, dibucaine, procaine, procaine amide and amino methyl benzoate," & JP 2004 339213 A ((ROHT) Rohto Seiyaku KK), Dec. 2, 2004.

* cited by examiner

*Primary Examiner* — Theodore R. Howell
(74) *Attorney, Agent, or Firm* — Merchant & Gould P.C.

(57) ABSTRACT

Provided herein are compositions and methods for treating or preventing a skin disease or skin condition on the skin of a subject by administering a topical flunisolide composition comprising a therapeutically effective amount of flunisolide and a solubilizing agent that solubilizes the flunisolide.

35 Claims, No Drawings

TOPICAL COMPOSITIONS OF FLUNISOLIDE AND METHODS OF TREATMENT

BACKGROUND OF THE INVENTION

Topical corticosteroids are useful for their anti-inflammatory, anti-pruritic, and vasoconstrictive actions. Flunisolide is the common name for the anti-inflammatory glucocorticosteroid, 6α-fluoro-11β, 21-dihydroxy-16α,17α-(isopropylidenedioxy)pregna-1,4-diene-3,20-dione, which has the following chemical structure:

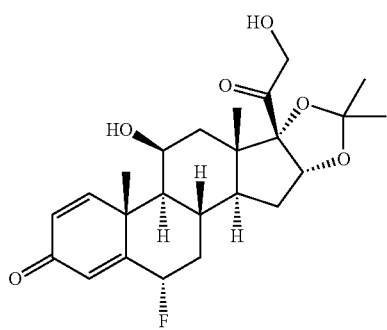

Flunisolide has demonstrated marked anti-inflammatory activity in classical test systems. It is a corticosteroid that is several hundred times more potent than cortisol in animal anti-inflammatory assays, and several hundred times more potent than dexamethasone in anti-inflammatory effects as determined by the McKenzie skin blanching test. Corticosteroids have been shown to have a wide range of anti-inflammatory effects, inhibiting both inflammatory cells and release of inflammatory mediators. It is presumed that these anti-inflammatory actions play an important role in the efficacy of flunisolide in controlling symptoms and improving lung function in asthma.

The synthesis and anti-inflammatory use of flunisolide is described in U.S. Pat. No. 3,126,375, which is hereby incorporated by reference. U.S. Pat. No. 4,933,168, which is incorporated by reference, discloses a hemihydrate form of flunisolide and an aerosol composition containing the hemihydrate form of flunisolide for use in the treatment of respiratory diseases such as bronchial asthma, allergic rhinitis, and other diseases that are responsive to treatment by suitable steroids.

U.S. Pat. No. 4,427,670, which is incorporated by reference, relates to a skin preparation containing flunisolide, phosphatide, and at least one of butylhydroxyanisole (BHA) and butylhydroxytoluene (BHT) to impart stability to the preparation for a prolonged period. EP Patent No. 0173478, which is incorporated by reference, discloses a topical composition for skin treatment containing an anti-inflammatory glucocorticoid, such as flunisolide, in combination with an essential fatty acid (EFA) of the n-6 or n-3 series or equivalent polyunsaturated fatty acids.

Skin diseases such as psoriasis, acne, dermatitis, eczema and lichen are frequently accompanied by inflammation, which can be mediated by a number of inflammatory cytokines secreted by inflammatory cells such as lymphocytes, macrophages, and by a number of locally or regionally acting substances, such as histamine, bradykinin, serotonin, prostaglandins, thromboxanes, leukotrienes, and platelet-activating factors. Topical corticosteroid-containing skin preparations have been used widely to treat such skin diseases.

However, there remains a need in the art for more effective and stable pharmaceutical compositions for treating skin diseases and conditions, such as psoriasis, dermatitis, acne, eczemas, wounds, burns, smoking/nicotine-induced damage, sun-induced damage and premature aging, as well as other conditions causing damage to the tissues through inflammation. The present invention fulfills this and other needs.

BRIEF SUMMARY OF THE INVENTION

Provided herein are compositions and methods for treating skin conditions in a subject by administering to the subject a topical composition comprising a therapeutically effective amount of flunisolide, or a salt thereof. Nonlimiting examples of skin conditions that can be treated using the compositions and methods disclosed herein include, but are not limited to, seborrheic or atopic dermatitis, localized neurodermatitis, anogenital pruritus, psoriasis, eczemas, late phase of allergic contact dermatitis, inflammatory phase of xerosis, acne, wounds, burns, smoking/nicotine-induced damage, sun-induced damage and premature aging, as well as other conditions causing damage to the tissues through inflammation.

In some embodiments, the topical composition is placed directly at the site of the skin condition. Importantly, it has been found that the topical compositions of the present invention result in little to no systemic exposure to flunisolide. As such, in some embodiments, the administration of the compositions do not result in substantial systemic exposure, i.e., systemic exposure to flunisolide is low. In other embodiments, the topical compositions do not result in systemic exposure of flunisolide.

In some embodiments, the flunisolide in the topical compositions is the anhydrous form, i.e., flunisolide anhydrous. In other embodiments, the flunisolide in the topical compositions is the hemihydrate form, i.e., flunisolide hemihydrate. In some embodiments, the flunisolide in the topical composition is substantially solubilized, i.e., greater than 90% of the flunisolide is solubilized.

In some embodiments, the topical composition is an emulsion, gel, cream, oil, ointment, paste, spray, or lotion. In some embodiments, the topical composition is a cream. In some embodiments, the cream is a cream emulsion with a mean droplet diameter between about 0.1 µm to about 100 µm. In some embodiments, the composition is in the form of a microemulsion or nanoemulsion, which helps to solubilize the flunisolide, especially when the resulting composition is in the form of a cream.

In some embodiments, the topical flunisolide compositions comprise one or more solubilizing agents, emulsifiers, emollients, preservatives, humectants, moisturizers, opacifiers, thickeners, pH modifiers and combinations thereof.

Typically, the amount of flunisolide present in the topical compositions is between about 0.01% to about 0.35%. In some embodiments, the amount of flunisolide present in the topical compositions is less than about 0.25% by weight of the compositions. In some embodiments, the amount of flunisolide present in the topical compositions is about 0.25% by weight of the compositions. In some embodiments, the amount of flunisolide present in the topical compositions is about 0.1% by weight of the compositions.

In various embodiments, the skin condition is a corticosteroid-responsive dermatosis, pruritis, psoriasis, seborrhea, contact dermatitis, rosacea, atopic dermatitis, an inflammation of the skin, or a combination thereof. In one specific example, the skin condition is psoriasis. In another specific example, the skin condition is atopic dermatitis. In yet another specific example, the skin condition is an inflammation of the skin.

In one aspect, the invention provides topical flunisolide compositions for treating a skin condition, the compositions comprising a therapeutically effective amount of flunisolide or a salt thereof; and a solubilizing agent that solubilizes the flunisolide. Solubilizing agents suitable for use in the compositions disclosed herein include, but are not limited to, benzyl alcohol, propylene glycol, polyethylene glycol 400, diethylene glycol monoethyl ether, dimethyl isosorbide, polyethylene glycol 7 methyl ether, dimethyl sulfoxide, propylene carbonate, isopropyl myristate, isopropyl alcohol, isopropyl isostearate, isopropyl palmitate, water and combinations thereof. In preferred embodiments, the solubilizing agent includes, but is not limited to, benzyl alcohol, propylene glycol, dimethyl isosorbide, diethylene glycol monoethyl ether, isopropyl alcohol, isopropyl myristate, polyethylene glycol 7 methyl ether, a mixture of isopropyl isostearate and isopropyl palmitate and a mixture of isopropyl myristate and benzyl alcohol.

In another embodiment, the compositions further comprise an emulsifying agent. Examples of emulsifying agent suitable for use in the topical compositions disclosed herein include, but are not limited to, polyoxyl 40 hydrogenated castor oil, vegetable oil hydrogenated, lecithin, steareth 2, glyceryl monostearate, glyceryl stearate/PEG 100 stearate, polyoxyl 20 cetostearyl ether, steareth-21, polysorbate 60, PPG 15 stearyl ether, sorbitan monostearate, sodium lauryl sulfate, polyethylene glycol monopalmitostearate, cetostearyl alcohol, cetyl alcohol, stearyl alcohol, cetyl esters wax, white petrolatum, caprylocaproyl polyoxy-8 glycerides and mixtures thereof.

In yet another embodiment, the compositions further comprise an emollient. Exemplary emollients suitable for use in the compositions disclosed herein include, but are not limited to, mineral oil, lanolin alcohol, octyldodecanol, oleyl alcohol, isosteric acid, oleic acid, isopropyl myristate, mediumchain triglycerides, olive oil, soybean oil, isopropyl palmitate, iosopropyl isostearate, propylene glycol dicaprylate, cocoyl caprylocarpate and mixtures thereof.

In still another embodiment, the compositions further comprise a humectant or a moisturizer or both. Exemplary humectants and moisturizers include, but are not limited to, glycerin, isopropyl isostearate, alkoxylated methyl glucose derivative, dimethicone 350, dimethicone 360 and cyclomethicone.

In a further embodiment, the compositions further comprise a preservative. Exemplary preservatives suitable for use in the compositions disclosed herein include, but are not limited to, methyl paraben, propyl paraben, diazodinyl urea and combinations thereof.

In still another embodiment, the compositions further comprise a thickening agent. Thickening agents suitable for use in the compositions disclosed herein include, but are not limited to, acrylate co-polymers (Pemulen™ TR-1), carbomer homopolymer Type C (Carbopol 980), sepineo P 600 and combinations thereof.

In still other embodiments, the compositions further comprise an anti-oxidant. Exemplary anti-oxidants suitable for use in the compositions disclosed herein include, but are not limited to, butylatedhydroxytoluene (BHT) and butylhydroxyanisole (BHA). In a preferred embodiment, the anti-oxidant is BHT.

In other embodiments, the compositions further comprise a chelating agent. Suitable chelating agents for use in the compositions disclosed herein include, but are not limited to, EDTA, Edetate disodium, etc.

In yet another embodiment, the compositions further comprise an opacifier, such as aluminum starch octenylsuccinate or titanium dioxide.

In certain embodiments, the compositions further comprise one or more of the following: an emulsifying agent, an emollient, a preservative, a chelating agent, an anti-oxidant, a thickener, a humectant, a moisturizer, an opacifier, a pH modifier and combinations thereof. In other embodiments, the compositions further comprise each of the following: an emulsifying agent, an emollient, a preservative, a chelating agent, an anti-oxidant, a thickener, a humectant/moisturizer, an opacifier, a pH modifier and combinations thereof.

In some embodiments, the topical flunisolide compositions are emulsions, gels, creams, oils, sprays, ointments, pastes or lotions. In some embodiments, the compositions are a cream. In some embodiments, the compositions are a microemulsion. In other embodiments, the compositions are a nanoemulsion.

In some embodiments, the topical flunisolide composition is selected from the compositions set forth in Tables 1-17, infra. In other embodiments, the topical flunisolide composition is selected from the compositions set forth in Tables 12-17, infra.

In yet another aspect, the present invention provides a method for treating a skin condition (or skin disorder or skin disease) of a subject, the method comprising administering to the subject a topical flunisolide composition as disclosed herein. In one embodiment, the topical composition is placed directly at the site of the skin condition. In another embodiment, the topical composition does not result in substantial systemic exposure of flunisolide. In still another embodiment, the flunisolide is substantially solubilized, i.e., greater than 90% of the flunisolide is solubilized, more preferably, greater than 93% of the flunisolide is solubilized, more preferably, greater than 95% of the flunisolide is solubilized, and more preferably, greater than 97% of the flunisolide is solubilized. In some embodiments, the composition is in the form of a microemulsion or nanoemulsion, which helps to solubilize the flunisolide, especially when the topical composition is in the form of a cream. In yet other embodiments, the topical composition is an emulsion, gel, cream, oil, ointment, spray, paste, or lotion. In a preferred embodiment, the topical composition is a cream. In another preferred embodiment, the topical composition is formulated for administration to the skin or scalp.

In some embodiments, the amount of flunisolide present in the topical composition is between about 0.01% to about 0.35% by weight of the composition. In other embodiments, the amount of flunisolide present in the topical composition is about 0.25% by weight of the composition. In another embodiment, the amount of flunisolide present in the topical composition is about 0.1% by weight of the composition.

In some embodiments, the skin condition includes, but is not limited to, seborrheic or atopic dermatitis, localized neurodermatitis, anogenital pruritus, psoriasis, eczemas, late phase of allergic contact dermatitis, inflammatory phase of xerosis, acne, wounds, burns, smoking/nicotine-induced damage, sun-induced damage and premature aging, as well as other diseases/conditions causing damage to the tissues through inflammation. In preferred embodiments, the skin condition is dermatosis, pruritis, psoriasis, seborrhea, contact dermatitis, rosacea, atopic dermatitis, an inflammation of the skin, or a combination thereof. In other preferred embodiments, the skin condition is psoriasis, atopic dermatitis or inflammation of the skin.

Provided herein are compositions for treating skin conditions comprising: a therapeutically effective amount of flunisolide or a salt thereof and a means for delivering the flunisolide or the salt thereof to the site of the skin condition. In some embodiments, the means for delivering the flunisolide to the site of the skin condition further comprises a solubilizing means for solubilizing the flunisolide. In some embodiments, the means for delivering the flunisolide to the site of the skin condition comprises at least one of: a solubilizing means for solubilizing the flunisolide, a preservative means for assuring chemical stability, an oleaginous (oil) means for creating an oil-in-water or water-in-oil emulsion, an emulsifying means for maintaining the emulsion, a thickening means for increasing the viscosity, a emollient means for establishing the physical properties of the embodiment, a chelating means for protecting against degradation by metal ions, an antioxidant means for protecting against degradation by exposure to air, or an antimicrobial means for protecting against microbiological contamination.

Also provided herein is a system for treating a skin condition on the skin of a subject comprising a means for topically delivering a therapeutically effective amount of flunisolide to the site of the skin condition. In various embodiments, the means for delivery is an emulsion, gel, cream, foam, oil, ointment, paste, spray or lotion comprising at least one of: a solubilizing means for solubilizing the flunisolide, a penetrant means for causing the flunisolide to penetrate the skin, a preservative means for assuring chemical stability, an oleaginous (oil) means for creating an oil-in-water or water-in-oil emulsion, an emulsifying means for maintaining an emulsion, a thickening or surfactant means for establishing the physical properties of the embodiment, a chelating means for protecting against degradation by metal ions, an antioxidant means for protecting against degradation by exposure to air, or an antimicrobial means for protecting against microbiological contamination.

Further provided herein is a system for treating a skin condition on the skin of a subject comprising a means for topically delivering a therapeutically effective amount of flunisolide, or a salt thereof, to the site of the skin condition. In one embodiment, the means for delivery is an emulsion, gel, cream, oil, spray, ointment, paste, or lotion.

These and other features, aspects, and embodiments are described below in the section entitled "Detailed Description of the Invention" as well as in Examples 1-17 and the claims that follow.

DETAILED DESCRIPTION OF THE INVENTION

Topical pharmaceutical formulations containing flunisolide as an active pharmaceutical ingredient (API) are disclosed. The flunisolide formulations are useful for treating skin conditions characterized at least in part by inflammation. It has surprisingly been found that the topical flunisolide compositions of the present invention have a number of advantages over other flunisolide compositions. For instance, the topical flunisolide compositions of the present invention contain flunisolide in the solubilized form. Preferably, greater than 90%, greater than 93%, greater than 95%, greater than 96%, greater than 97%, greater than 98% or greater than 99% of the flunisolide is in the solubilized form. In addition, the topical flunisolide compositions of the present result in very low or no systemic exposure to flunisolide. Moreover, the topical flunisolide compositions of the present invention are very stable upon storage. Preferably, there is little or no change in the amount of flunisolide in the topical compositions of the present invention upon storage.

As such, the present invention relates to topical flunisolide compositions and to methods for treating skin conditions of a subject by administering to the subject in need thereof the topical compositions that comprise a therapeutically effective amount of flunisolide, or a salt thereof, and a solubilizing agent. Nonlimiting examples of skin diseases and skin conditions that can be treated using the compositions and methods disclosed herein include, but are not limited to, psoriasis, dermatitis, acne, eczemas, wounds, burns, smoking/nicotine-induced damage, sun-induced damage and premature aging, as well as other conditions causing damage to the tissues through inflammation.

Exemplary Definitions

As used herein, the term "topical application" refers to an application onto external body surfaces, such as the skin and hair, excluding the mucosal application. Exemplary topical dosage forms include, but are not limited to: emulsions, liniments, balms, foams, gels, creams, aqueous solutions, oils, sprays, ointments, pastes, shampoos and conditioners, lotions, or suspensions.

The terms "treat" or "treating", and other grammatical equivalents as used herein, include alleviating, abating, or ameliorating a disease or condition or one or more symptoms thereof, preventing additional symptoms, ameliorating or preventing the underlying metabolic causes of symptoms, inhibiting the disease or condition (for example, arresting the development of the disease or condition), relieving the disease or condition, causing regression of the disease or condition, relieving a condition caused by the disease or condition, or stopping the symptoms of the disease or condition, and are intended to include prophylaxis uses of the flunisolide compositions disclosed herein.

The term "therapeutically effective amount," as used herein, refers to a sufficient amount of flunisolide being administered that will relieve to some extent one or more of the symptoms of the skin condition being treated. The result can be reduction and/or alleviation of the signs, symptoms, or causes of a disease, or any other desired alteration of a biological system. An appropriate "therapeutically effective amount" may differ from one individual to another and may be readily determined by skilled artisans using techniques known in the art.

The term "pharmaceutically acceptable" means that the excipient meets the required standards of toxicological, manufacturing and testing.

The term "optionally" means that the subsequently described component may or may not be present, so that the description includes instances where the component is present and instances where it is not.

"Topical delivery," as used herein, refers to the application of a drug containing formulation to the skin to directly treat cutaneous disorders (e.g., acne) or the cutaneous manifestations of a general disease (e.g., psoriasis) with the intent of exerting the pharmacological or other effect of the drug to the surface of the skin or within the skin. Topical delivery includes various pharmaceutical dosage forms such as ointments, creams, patches, gels, topical sprays and lotions.

In this disclosure, the use of the singular can include the plural unless specifically stated otherwise or unless, as will be understood by one of skill in the art in light of this disclosure, the singular is the only functional embodiment. For example, "a" can mean more than one, and "one embodiment" can mean that the description applies to multiple embodiments. Additionally, in this disclosure, "or" denotes that both the inclusive and exclusive meanings of "or" (as denoted by the term "and/or") and does not solely encompass the exclusive meaning of "or" unless clearly denoted to be exclusive. Thus, the listing should be read to include all possible combinations of the items of the list and to also include each item, exclusively, from the other items. The meaning of such terms will be evident to one of skill in the art upon reading the particular disclosure.

As will be appreciated by one of skill in the art, while this specification may simply use one of the terms "comprise," "consists," or "consists essentially of", this is simply a shorthand way of describing all three possibilities, unless otherwise specified or unless the term is used in the claim (in which case the terms will have their normally accepted meanings under claim interpretation). Thus, as the terms are used above, they designate all three possibilities, unless explicitly noted otherwise.

The terms "approximately, "about," and "substantially" as used herein represent an amount close to the stated amount that still performs the desired function or achieves the desired result. For example, the terms "approximately", "about", and "substantially" may refer to an amount that is within less than 10% of, within less than 5% of, within less than 1% of, within less than 0.1% of, or within less than 0.01% of the stated amount.

All weight percentages recited herein are based on the total weight of the composition unless otherwise indicated.

Exemplary Topical Flunisolide Compositions

Nonlimiting examples of topical flunisolide compositions useful in the invention are provided herein. In addition to flunisolide, the compositions disclosed herein may contain additional components known in the art to be useful in topical pharmaceutical or cosmetic formulations. Nonlimiting examples of these additional components include solvents, solubilizing agents, penetrants, emulsifiers, thickeners, oils, emollients, surfactants, chelating agents, antioxidants, preservatives, colorants, and perfumes.

Flunisolide

In the compositions useful in the invention described herein, flunisolide, or a salt thereof, is present in a pharmaceutically accessible form suitable for skin absorption, including but not limited to a solubilized form and/or a crystalline form.

In some embodiments, the amount of flunisolide present in the composition in a pharmaceutically accessible form for skin absorption is high. For example, at least about: 90%, 91%, 92%, 93%, 94%, 95%, 96%, 97%, 98%, or 99% of the flunisolide present in the topical composition is in a pharmaceutically accessible form for skin absorption.

In some embodiments, the flunisolide present in the composition is substantially solubilized, i.e., all is solubilized, or less than about 5% is not solubilized. In some embodiments, the flunisolide present in the composition is substantially solubilized, i.e., all is solubilized, or less than about 3% is not solubilized. In some embodiments, the flunisolide present in the composition is substantially solubilized, i.e., all is solubilized, or less than about 1% is not solubilized. Thus, in the compositions of the present invention, For example, at least about: 90%, 91%, 92%, 93%, 94%, 95%, 96%, 97%, 98%, or 99% of the flunisolide present in the topical composition is solubilized, i.e., is in the solubilized form.

In some embodiments, the solubilized flunisolide is in the form of an emulsion. In some embodiments, the solubilized flunisolide is in the form of a microemulsion or a nanoemulsion.

As will be appreciated by those of skill in the art, the total amount of flunisolide in the compositions can vary. For example, the total amount of flunisolide in the composition can be between about 0.001% to about 5%. In some embodiments, the amount of flunisolide in the composition is between about 0.0025% and about 0.05%. In some embodiments, the amount of flunisolide is about 0.01% to about 0.25%. In some embodiments, the amount of flunisolide is about 0.25%, or less. In an aspect, the amount of flunisolide in the composition is about 0.1%. In another aspect, the amount of flunisolide in the composition is about 0.05% and 0.25%. According to embodiments, the amount of flunisolide in the composition is about: 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, or any range between any two of these values. In some embodiments, the amount of flunisolide in the composition is less than about: 0.5%, 0.45%, 0.4%, 0.35%, 0.3%, 0.25%, 0.2%, 0.15%, 0.1% or 0.05%.

In preferred embodiments, the flunisolide is generally present in the compositions and methods disclosed herein in a therapeutically effective amount, i.e., an amount of flunisolide such that when delivered to the site of a skin condition of a subject, the composition brings to bear the intended therapeutic action. In some preferred embodiments, flunisolide constitutes between about 0.01% to about 0.35% by total weight of the composition and, more preferably, between about 0.05% to about 0.25% by total weight of the composition. In one aspect, the amount of flunisolide in the composition is about 0.1% or about 0.25%.

According to embodiments, the composition has a weight ratio of flunisolide in a solubilized form and flunisolide in a crystalline form of at least about 99:1, 98:2 or 97:3. According to embodiments, the composition has a weight ratio of flunisolide in a solubilized form and flunisolide in a crystalline form of at least about 96:4, 95:5, 94:6, 93:7, 92:8 or 91:9. According to embodiments, the composition has a weight ratio of flunisolide in a solubilized form and flunisolide in a crystalline form of at least about between 90:10 and 80:20. According to still other embodiments, the composition has a weight ratio of flunisolide in a solubilized form and flunisolide in a crystalline form of at least about between 80:20 and 50:50. In other aspects, the composition has a weight ratio of flunisolide in a solubilized form and flunisolide in a crystalline form of less than 50:50.

In some embodiments and depending on the formulation selected, the composition has an amount of flunisolide in a crystal form of less than about: 50%, 40%, 30%, 20%, 10%, 9%, 8%, 7%, 6%, 5%, 4%, 3%, or 2%; or 1%. According to embodiments, the composition has an amount of flunisolide in a crystal form of greater than 50%, and as high as 90%.

According to other embodiments, the amount of flunisolide in a solubilized form in an upper-solubilization range is at least about 97%-99%. According to other embodiments, the amount of flunisolide in a solubilized form in a mid-solubilization range is at least about 94%-96%. According to other embodiments, the amount of flunisolide in a solubilized form in a lower-solubilization range is at least about 90%-93%. The present invention provides topical flunisolide compositions in the upper-solubilization range, the mid-solumbilzation range and the lower-solubilization range. In certain embodiments, the topical flunisolide compositions are in the upper-solubilization range.

Exemplary Topical Dosage Forms

Flunisolide compositions disclosed herein can be in any form suitable for topical application of a drug. Nonlimiting examples of topical dosage forms include emulsions, liniments, balms, foams, gels, creams, aqueous solutions, oils, sprays, ointments, pastes, shampoos and conditioners, lotions, suspensions, and any combinations thereof. Thus, means for topically delivering flunisolide to the site of a skin condition include, but are not limited to, compositions in the form of an emulsion, liniment, balm, foam, gel, cream, aqueous solution, oil, spray, ointment, paste, shampoo and conditioner, lotion, or suspension.

In some embodiments, the composition is in a topical cream dosage form, a topical ointment dosage form and a topical gel dosage form.

As one of skill in the art will appreciate, creams are semisolid water-in-oil (W/O) or oil-in-water (O/W) emulsions that serve to soften the skin. Creams are easy to spread, are nongreasy, light, have a cooling effect on the skin, are easy to wash off with water and do not stain clothing. Creams are particularly advantageous when the emulsion is to be applied to a part of the body covered by hair, such as the scalp, legs, arms, chest, etc. The choice of O/W or W/O emulsions for preparations applied to the skin depends on several factors. Medications that are irritating to the skin are better tolerated if they are applied to the skin as small particles present in the internal phase. The external phase keeps them from directly contacting and irritating the skin. Therefore, medications that dissolve more readily in oil are applied to the skin as O/W emulsions, in which the oil is in the internal phase, while those that dissolve in water are applied as W/O emulsions, in which the water is the internal phase. W/O cream emulsions can be spread on unbroken skin. They spread more evenly than O/W emulsions since the natural oils on the skin readily mix with the external oil phase of the emulsion.

Also, as one of skill will appreciate, lotions are suspensions intended for external applications. They contain finely powdered medications, and they cool, soothe, dry, or protect the skin. Lotions are usually applied without rubbing and work easily into large areas of the skin without leaving a greasy or oily feeling.

Gels are a dimensionally stable, easily deformable, liquid and optionally gas-rich, dispersed system that consists of at least two components. Gels are similar to magmas and milks except that the suspended particle size in gels is smaller.

Ointments are semisolid medication dosage forms intended to be applied to the skin or mucous membranes. They are used to lubricate and soften or as a base (a vehicle that contains a drug) for drug delivery. Some medications may be more stable or more readily absorbed by the skin when delivered in some types of ointment bases over others.

Again, in the context of this disclosure, the novel topical compositions of flunisolide can be, for example, in the form of a gel, cream, ointment, emulsion, suspension, solution, drops, lotion, paint, pessary, douche, suppository, troche, spray, sponge, film, patch, or foam. The topical compositions of flunisolide are intended for local application to an afflicted region of a subject. Preferably, the stable topical composition is in the form of a cream, gel or an ointment.

Exemplary Pharmaceutically Acceptable Excipients

The flunisolide compositions disclosed herein may contain additional components or pharmaceutically acceptable excipients known in the art to be useful in topical pharmaceutical or cosmetic formulations. Nonlimiting examples of these pharmaceutically acceptable excipients include solubilizers, emulsifiers, emollients, buffers, preservatives, thickening agents, moisturizers, stabilizers, anti-foaming agents, alkalizers/neutralizers and vehicles. It will be understood by those of skill in the art that one excipient can perform more than one function. The topical flunisolide compositions of this disclosure can be prepared by procedures well known to those skilled in the art.

Exemplary Solvents/Co-Solvents & Emulsifiers

The compositions disclosed herein comprise one or more solubilizing agents or solvents for solubilizing the flunisolide. Pharmaceutically acceptable solubilizing agents/solvents for use in the topical compositions disclosed herein include, but are not limited to, glycerin, propylene glycol, water, hexylene glycol, polysorbate 60, polyglyceryl-3-oleate, sorbitol solution, white petrolatum, xanthan gum, cetomacrogol 1000, polyethylene glycol (PEG) (e.g., polyethylene glycol 400), cyclomethicone, demethiconol, dimethicone copolyol, hydroxyoctacosanyl hydroxy stearate, methoxy PEG-22/dodecylglycol copolymer, Carbomer 940, docusate sodium, trolamine NF, Carbomer 934P, poloxamer 407, triolein, diethylene glycol monoethyl ether, benzyl alcohol, cetostearyl alcohol, dimethyl isosorbide, dimethyl sulfoxide, PEG-7 methyl ether, propylene carbonate, isopropyl palmitate, isopropyl isostearate, isopropyl myristate and isostearic acid. The solvent/solubilizers may be incorporated into the compositions in an amount of about 3% w/w to about 75% w/w based on the total weight of the composition. The desired quantity will depend on the intended use and the desired formulation characteristics.

In preferred embodiments, the composition comprises one or more solubilizing agent(s)/solvent selected from the following: benzyl alcohol, propylene glycol, polyethylene glycol 400, diethylene glycol monoethyl ether, dimethyl isosorbide, polyethylene glycol 7 methyl ether, dimethyl sulfoxide, propylene carbonate, isopropyl myristate, isopropyl alcohol, isopropyl isostearate, isopropyl palmitate, water and combinations thereof.

In preferred embodiments, the composition comprises one or more solubilizing agent(s)/solvent selected from the following: benzyl alcohol, propylene glycol, dimethyl isosorbide, diethylene glycol monoethyl ether, isopropyl alcohol, isopropyl myristate, polyethylene glycol 7 methyl ether, a mixture of isopropyl isostearate and isopropyl palmitate and a mixture of isopropyl myristate and benzyl alcohol. In some embodiments, the solubilizing agent is benzyl alcohol.

Emulsifying agents reduce the surface tension of two phases in an emulsion, thereby preventing coalescence of the individual phases. In some embodiments, the composition comprises one or more emulsifier(s). Pharmaceutically acceptable emulsifying agents, i.e., emulsifiers, suitable for use in the topical compositions disclosed herein include, but are not limited to, polyoxyethylene oleyl ether, PEG-40 stearate, ceteareth-12, Eumulgin B-1 (Henkel), ceteareth-20, Eumulgin B-2 (Henkel), ceteareth-30, Lanette O (Henkel), glyceryl monostearate, glyceryl stearate, caprylocaproyl polyoxy-8 glycerides (Labrasol), Cutina GMS (Henkel), PEG-100 stearate, methyl myristate, isopropyl myristate, Arlacel 165, PEG-100 stearate, steareth-2, steareth-20, steareth-21, dimethicone copolyol, Polysorbate 20 (Tween 20), Polysorbate 40 (Tween 40), Polysorbate 60 (Tween 60), Polysorbate 80 (Tween 80), lauramide DEA, cocamide DEA, and cocamide MEA, alginate, carrageenan, Glucate DO, methylcellulose, polyvinyl alcohol, cocamidopropyl phosphatidyl PG-dimonium chloride, Pemulen TR 1, Pemulen TR 2, Carbomer 1342, Carbomer 980, Carbomer 1382, Carbomer 1342, Carbomer 934, white wax, Carbomer 934P, Carbomer 940, Carbomer 941, Carbomer 974P, Carbomer 980, and diisopropanolamine, PEG 7 methyl ether, Carbomer 981, polyoxyl 40 hydrogenated castor oil, vegetable oil hydrogenated, lecithin, glyceryl monostearate, glyceryl stearate/PEG 100 stearate, polyoxyl 20 cetostearyl ether, PPG 15 stearyl ether, sorbitan monostearate, sodium lauryl sulfate, polyethylene glycol monopalmitostearate and mixtures thereof. The emulsifier(s) can be incorporated into the compositions in an amount of about 0.05% w/w to about 25% w/w based on the total weight of the composition. The desired quantity will depend on the intended use and the desired formulation characteristics.

In preferred embodiments, the composition comprises one or more emulsifier(s) selected from the following: polyoxyl 40 hydrogenated castor oil, vegetable oil hydrogenated, lecithin, steareth 2, glyceryl monostearate, glyceryl stearate/PEG 100 stearate, polyoxyl 20 cetostearyl ether, steareth-21, caprylocaproyl polyoxy-8 glycerides, polysorbate 60, PPG 15 stearyl ether, sorbitan monostearate, sodium lauryl sulfate, polyethylene glycol monopalmitostearate and mixtures thereof.

In some embodiments, the emulsifying agent is also a stiffening agent. Nonlimiting examples of emulsifying/stiffening agents include, but are not limited to, cetosteary alcohol, cetyl alcohol, stearyl alcohol, white wax (cetyl esters wax), white petrolatum and mixtures thereof. In certain embodiments, in addition to the emulsifying/stiffening agent, the compositions disclosed herein may also comprise one or more solvent/solubilizing agent and one or more emulsifying agents that are not also stiffening agents.

Pharmaceutically acceptable emulsion stabilizers suitable for use in the topical compositions disclosed herein include, but are not limited to, glyceryl monostearate, with or without stearic acid, cetyl alcohol, stearyl alcohol or mixtures thereof and cetomacrogol 1000. The emulsion stabilizers may be incorporated into the compositions in an amount of about 1% w/w to about 15% w/w based on the total weight of the composition. The desired quantity will depend on the intended use and the desired formulation characteristics.

In some embodiments, the composition is an emulsion and the droplet diameter of the emulsion is between about 0.1 μm to about 100 μm. In some embodiments the composition is a water-in-oil emulsion and comprises an oleaginous base; less than 45% by weight water; and a surfactant with a hydrophilic-lipophilic balance of less than or equal to about 8. In some embodiments, the composition is an oil-in-water emulsion and comprises an oleaginous base, more than 45% by weight water, and a surfactant with a hydrophilic-lipophilic balance of greater than or equal to about 9.

Exemplary Emollients

In some embodiments, the composition comprises one or more emollient(s). Nonlimiting examples of emollients suitable for use in the topical compositions of the instant invention include mineral oil, lanolin alcohol, octyldodecanol, oleyl alcohol, isosteric acid, oleic acid, isopropyl myristate, mediumchain triglycerides, olive oil, soybean oil, isopropyl palmitate, iosopropyl isostearate, propylene glycol dicaprylate, cocoyl caprylocarprate and mixtures thereof. The emollients may be incorporated into the compositions in an amount of about 1% w/w to about 45% w/w based on the total weight of the composition. The desired quantity will depend on the intended use and the desired formulation characteristics.

In some embodiments, the composition is a cream and the total amount of emollient in the cream is between about 5% to 30%, or between about 5% to 10%.

Exemplary Preservatives & Chelating Agents

Preservatives prevent or slow microbial growth and typically fall into one of four major compound types as follows: acids, alcohols, quaternary ammonium compounds, or organic mercurial compounds. Chelating agents have the ability to bind metal ions and prevent auto-oxidation, a phenomenon frequently catalyzed by metal ions, and at the same time enhance the action of preservatives by binding iron and copper ions essential to microbial growth.

In some embodiments the composition comprises one or more preservative(s). Nonlimiting examples of preservatives include chloro-m-cresol, citric acid, imidurea, disodium edetate, ethoxylated alcohol, glycerin, 1,2,6-hexanetriol, parabens, potassium sorbate, propyl gallate, propylene glycol, sodium bisulfite, sodium citrate, sodium metabisulfite, sorbic acid, tannic acid, zinc stearate, butylated hydroxytoluene, benzoic acid, salicylic acid, dichlorobenzyl alcohol, formaldehyde, alpha-tocopherol, sodium ascorbate, ascorbic acid, ascorbyl palmitate phenol, m-cresol, bisphenol, cetrimide, imidurea, benzalkonium chloride, sorbic acid, polyquaternium-1, chlorobutanol, chlorhexidine, Dowcell 200 (Dow Chemical Co), Glydant (dimethylol-25,5-dimethylhydantoin, Lonza, Inc), Germal 115 (imidazolidylurea, Sutton Laboratories), Germal II (diazolidinylurea, Sutton Laboratories), sodium hydroxymethylglycinate, Buzan 1504 (dimethhydroxymethylpyrazole, Buckman Labs), phenoxyethanol, chlorocresol, benzoyl peroxide, methylchloroisothiazoline, methylisothiazoline, benzyl alcohol or mixtures thereof. The preservatives may be incorporated into the compositions in an amount of about 0.0001% w/w to about 5.0% w/w based on the total weight of the composition. The desired quantity will depend on the intended use and the desired formulation characteristics.

In preferred embodiments, the composition comprises one or more preservative(s) selected from the following: methylparaben, propylparaben, diazodinyl urea, methylchloroisothiazolinone, methylisothiazolinone and mixtures thereof. The appropriate amount of preservative useful in these compositions is known by, readily available to or determined by those skilled in the art.

In some embodiments, a chelating agent is included in the composition. Nonlimiting examples of chelating agents include ethylenediaminetetraacetic acid (EDTA), ethylenediamine, porphine, heme, nitrilotriacetic acid, and citric acid. The appropriate amount of a chelating agent useful in these compositions is known by or readily available to those skilled in the art.

In some embodiments, the composition comprises one or more chelating agent(s) selected from EDTA, citric acid and combinations thereof.

Exemplary Thickening Agents

Thickening agents may be natural, semi-synthetic or synthetic and are used to increase viscosity of the composition. In some embodiments, the composition comprises one or more thickener(s) or thickening agent(s).

Pharmaceutically acceptable thickening agents suitable for use in the topical compositions of the instant invention include, but are not limited to, sodium alginate, xanthan gum, carrageenans, acacia, agar, gum tragacanth, carboxypolymethylene, polyvinylpyrrolidone, polyacrylamide, cellulosic polymers, carbomers and mixtures thereof. The thickening agents may be incorporated into the compositions in an amount of about 0.05% w/w to about 15% w/w based on the total weight of the composition. The desired quantity will depend on the intended use and the formulation characteristics.

In preferred embodiments, the composition comprises one or more thickener(s) selected from the following: acrylate co-polymers (Pemulen™ TR-1), carbomer homopolymer Type C (Carbopol 980), sepineo P 600 and mixtures thereof.

In some embodiments the composition is a cream and the total amount of thickener is up to about 30%. In some embodiments the amount of thickener is between about 3% to 12%.

Exemplary Stabilizers/Anti-Oxidants

Stabilizers are used to keep a formulation stable under various conditions. In some embodiments, the composition comprises one or more stabilizers. Nonlimiting examples of stabilizers include anti-oxidants such as tocopherol and butylated hydroxyl toluene, or reducing agents such as ascorbic acid.

In some embodiments, the composition comprises an anti-oxidant selected from BHA and BHT.

The appropriate amount of an anti-oxidant useful in these compositions is known by or readily available to those skilled in the art.

Moisturizers/Skin Conditioners/Humectants

In some embodiments the composition comprises one or more moisturizer(s), skin conditioner(s) or humectant(s).

Pharmaceutically acceptable moisturizers suitable for use in the topical compositions of the instant invention include, but are not limited to, the dimethicones, including Dimethicone 360, Dimethicone 350 and cyclomethicone. The moisturizers may be incorporated into the compositions in an amount of about 0.01% w/w to about 15% w/w based on the total weight of the composition. The desired quantity will depend on the intended use and the desired formulation characteristics.

Pharmaceutically acceptable skin conditioners or humectants suitable for use in the topical compositions of the instant invention include, but are not limited to, alkoxylated methyl glucose derivative, glycerin and isopropyl isostearate. The skin conditioners or humectants may be incorporated into the compositions in an amount of about 1% w/w to about 40% w/w based on the total weight of the composition. The desired quantity will depend on the intended use and the desired formulation characteristics.

Gelling Agents

In some embodiments, the composition disclosed herein is a gel and, thus, it comprises one or more gelling agent(s). Pharmaceutically acceptable gelling agents suitable for use in the topical compositions of the instant invention include, but are not limited to, synthetic macromolecules (e.g., carbomers, polyvinyl alcohols and polyoxyethylene-polyoxypropylene copolymers), gums such as tragacanth, sodium alginate, gelatin, methylcellulose, sodium carboxymethylcellulose, methylhydroxyethyl cellulose and hydroxyethyl cellulose. In order to prepare a uniform gel, dispersing agents such as alcohols or glycerin can be added, or the gelling agent can be dispersed by trituration, mechanical mixing or stirring, or combinations thereof. The gelling agents may be incorporated into the compositions in an amount of about 0.1% w/w to about 15% w/w based on the total weight of the composition. The desired quantity will depend on the intended use and the desired formulation characteristics.

Anti-Foaming Agents

In some embodiments the compositions disclosed herein comprise one or more anti-foaming agent(s). Pharmaceutically acceptable anti-foaming agents suitable for use in the topical compositions of the instant invention include, but are not limited to, simethicone, dimethicone, ethanol and ether. The anti-foaming agents may be incorporated into the compositions in an amount of about 0.5% w/w to about 5% w/w based on the total weight of the composition. The desired quantity will depend on the intended use and the desired formulation characteristics.

Exemplary Buffers

Pharmaceutically acceptable buffers suitable for use in the topical compositions of the instant invention include, but are not limited to, sodium citrate, potassium citrate, aluminum hydroxide, magnesium hydroxide, an alkali metal hydroxide or mixtures thereof. The buffers may be incorporated into the compositions in an amount of about 0.05% w/w to about 5% w/w based on the total weight of the composition. The desired quantity will depend on the intended use and the formulation characteristics.

Exemplary Acids

Pharmaceutically acceptable acids suitable for use in the topical compositions of the instant invention include, but are not limited to, maleic acid, fumaric acid, methanesulfonic acid, hydrochloric acid, sulfuric acid, nitric acid, oxalic acid, malonic acid, tartaric acid, malic acid, ethylenediamine tetraacetic acid, gluconic acid, glycine, lactic acid, citric acid or mixtures thereof. The acids may be incorporated into the compositions in an amount of about 0.05% w/w to about 5% w/w based on the total weight of the composition. The desired quantity will depend on the intended use and the formulation characteristics.

Exemplary Alkalizers/Neutralizers

Pharmaceutically acceptable alkalizers/neutralizers suitable for use in the topical compositions of the instant invention include, but are not limited to, triisopropanolamine, diisopropanolamine, isopropanolamine and triethanolamine. The alkalizers/neutralizers may be incorporated into the compositions in an amount of about 0.001% w/w to about 15% w/w based on the total weight of the composition. The desired quantity will depend on the intended use and the formulation characteristics.

Exemplary Vehicles

Pharmaceutically acceptable vehicles suitable for use in the topical compositions of the instant invention include, but are not limited to, water, alcoholic solvents, hydroalcoholic solvents, glycol based solvents, natural oils, synthetic oils, medium chain triglycerides and white petrolatum. The vehicles may be incorporated into the compositions in an amount of about 5% w/w to about 95% w/w based on the total weight of the composition. The desired quantity will depend on the intended use and the desired formulation characteristics.

In preferred embodiments, the composition comprises water as the vehicle, and the water is present in the formulation q.s. to 100, i.e., quantity sufficient to have a 100% of the formulation.

Opacifiers

In some embodiments, the compositions of the present invention further comprise an opacifier. Examples of opacifiers that are suitable for use in the present invention include, but are not limited to, aluminum starch octenylsuccinate and titanium dioxide. When present, the opacifier may be incorporated into the compositions in an amount of about 0.5% w/w to about 10% w/w.

Stability

The pH value of the compositions disclosed herein can vary. For example, the pH value of the composition can be about: 4, 5, 6, 7, or 8. In some embodiments, the pH value of the composition is between about 5 and 7. Citric acid, sodium citrate, sodium hydroxide and triethanolamine can, for example, be used to adjust pH, according to embodiments.

The stability of the compositions disclosed herein can be measured in terms of the amount of flunisolide or the amount of flunisolide-related impurities upon a period of storage of the composition under specified temperature and relative humidity (RH) conditions. In some embodiments, the compositions are physically or chemically stable after storage for a set period of time under specific temperature and relative humidity (RH), or specific number of freeze-thaw cycles. In some embodiments, a composition is considered stable when the change in the amount of flunisolide is no more than 10% for a set period of time under a specified temperature and relative humidity. The set period of time can be about 3 to 12 months. According to embodiments, the set period can go longer than a year, for example 15, 18, 21, or 24 months. Set periods of longer than two years are likewise included.

In some embodiments, the change in the amount of flunisolide in the composition is no more than about 10% after six months storage at 40° C. and 75% relative humidity. In some embodiments, the change in the amount of flunisolide in the composition is no more than about 10% after 2 years storage at 25° C. and 60% relative humidity. In some embodiments, the change in the amount of flunisolide in the composition is no more than 10% after six months storage at 40° C. and 75% relative humidity, and 2 years storage at 25° C. and 60% relative humidity. In some embodiments, the change in the amount of flunisolide in the composition is no more than about 10% after 1, 2, or 3 freeze-thaw cycles. In some embodiments, the free-thaw cycles include storage at about −10° C. to about −20° C. for between 3 to 4 days and storage at about 40° C. for between 3 to 4 days.

Exemplary Method of Treating Skin Conditions

Provided herein are methods for treating a skin condition on the skin of a subject in need thereof using the compositions described herein. In some embodiments, the method includes administering an effective amount of the flunisolide containing composition to a subject suffering from a skin condition. A skilled artisan is able to determine and use an appropriate amount of flunisolide to prevent or lessen side effects that may occur, such as toxicity or skin irritation.

Exemplary Skin Conditions

Nonlimiting examples of skin conditions treatable by the invention described herein include dermatosis, pruritis, psoriasis, seborrhea, contact dermatitis, rosacea, atopic dermatitis, acne, eczemas, wounds, burns, smoking/nicotine-induced damage, sun-induced damage and premature aging and any combinations thereof. Other skin conditions treatable by the invention described herein include inflammation as well as other conditions causing damage to the tissues through inflammation. In some other specific embodiments, the skin condition is psoriasis. In some other specific embodiments, the skin condition is mild or severe dermatosis. In yet other specific embodiments, the skin condition is an inflammation of the skin.

In some embodiments, the skin condition is psoriasis. Psoriasis is a T cell-mediated inflammatory disease which affects the skin and joints, usually causing red, scaly psoriatic patches to appear on the skin. The scaly patches caused by psoriasis, called psoriatic plaques, are areas of inflammation and excessive skin production. Fingernails and toenails are frequently affected. Psoriasis is considered to be one of the most common autoimmune diseases. In some embodiments, the psoriasis is chronic psoriasis.

In some embodiments, the skin condition is atopic dermatitis. Atopic dermatitis is a reaginically (IgE) associated, chronic disease of the skin. In people with atopic dermatitis, the skin is dry, easily irritated, subject to immediate hypersensitivity type of allergic responses, typically scaly, often thickened, commonly red, frequently infected, sometimes exudative, and itchy. In some embodiments, the atopic dermatitis is mild or severe atopic dermatitis.

The methods of application of the compositions can vary depending on the intended use. The compositions can be applied locally to the area affected by the skin condition, including but not limited to, the face, throat, arm(s), leg(s), hand(s), chest or scalp. In some embodiments, the compositions can be applied to the entire body.

In some embodiments, the administration of the composition for any indication does not result in substantial systemic exposure of flunisolide, i.e., the systemic exposure is low, for example under 5%. In some embodiments, a wide range for the amount of flunisolide in the composition that is systemically absorbed after administration to a patient is between about 0.01% to 50%. In some embodiments, less than about 50% of the flunisolide in the composition is absorbed systemically after administration to a patient, for example less than about: 40%, 35%, 30%, 25%, 20%, 15%, 10%, 5%, or 1%. In some embodiments, a range for the amount of flunisolide in the composition that is systemically absorbed after administration to a patient is between about 0.01% to 25%. In some embodiments, a range for the amount of flunisolide in the composition that is systemically absorbed after administration to a patient is between about 0.01% to 15%. In some embodiments, a range for the amount of flunisolide in the composition that is systemically absorbed after administration to a patient is between about 0.01% to 10%. In some embodiments, a range for the amount of flunisolide in the composition that is systemically absorbed after administration to a patient is between about 0.01% to 5%. In some embodiments, a range for the amount of flunisolide in the composition that is systemically absorbed after administration to a patient is between about 0.01% to 2%.

Exemplary Treatment Schedules

The flunisolide compositions disclosed herein can may be applied to the skin on an as-needed basis, or according to a pre-set schedule. The compositions can be applied directly to clean skin, before application of any other cosmetic or pharmaceutical composition(s). Alternatively, the compositions can be applied over the other cosmetic or pharmaceutical composition(s). The amount applied each time, the area of application, the duration of application, and the frequency of application can vary widely, depending on the specific need of the user. For example, the compositions can be applied for a period of days to months or even years, and at a frequency ranging from once a week, once a day to 5 times a day.

In some embodiments, a composition is applied from three to seven days a week and once, twice, or three times per each day of dosing for a period of 1 to 12 weeks to treat the skin condition. In some embodiments, formulations containing between about 0.1% and 0.25% flunisolide are favored.

While certain embodiments have been described above, it will be understood that the embodiments described are examples only. Accordingly, the systems and methods described herein should not be limited based on the described embodiments. Rather, the compositions, systems, and methods described herein should only be limited in light of the claims that follow when taken in conjunction with the above description.

EXAMPLES

Example 1: Topical Flunisolide Compositions

According to specific embodiments, topical flunisolide compositions for delivery of flunisolide to the site of a skin condition can comprise:

TABLE 1

| Ingredient | % w/w |
|---|---|
| Flunisolide | 0.05 to 0.25 |
| Benzyl alcohol | 0.1 to 1 |
| Propylene glycol | 25 to 75 |
| Cetostearyl alcohol | 3 to 12 |
| Citric acid anhydrous | 0.05 to 1 |
| Glyceryl monostearate | 1 to 10 |
| Glyceryl stearate & PEG 100 stearate | 1 to 10 |
| Sodium citrate anhydrous | 0.05 to 1 |
| White wax | 1 to 5 |
| Purified water | q.s to 100 |

Manufacturing Procedure:

Flunisolide is dissolved in benzyl alcohol under stirring or heating up to 45° C.-50° C.

Citric acid and sodium citrate are dissolved in a mixture of purified water and propylene glycol and heated up to 60° C.-65° C. to constitute aqueous phase.

The oily phase components, i.e., a mixture of cetostearyl alcohol, glyceryl monostearate, glyceryl stearate, PEG 100 stearate and white wax, are melted at 60° C.-65° C. and mixed well. The drug solution is added to the oily phase.

The oily phase containing the drug solution is added to aqueous phase under homogenisation for 10 to 15 minutes and cooled to room temperature under stirring.

Example 2: Topical Flunisolide Compositions

According to other specific embodiments, topical flunisolide compositions for delivery of flunisolide to the site of a skin infection or other skin condition on the skin can comprise:

TABLE 2

| Ingredient | % w/w |
|---|---|
| Flunisolide | 0.05 to 0.25 |
| Cetostearyl alcohol | 5 to 15 |
| Isopropyl myristate | 10 to 45 |
| Propylene glycol | 10 to 50 |
| Cetomacrogol 1000 | 1 to 10 |
| Dimethicone 350 | 1 to 10 |
| Citric acid | 0.05 to 1 |
| Sodium citrate | 0.05 to 1 |
| Benzyl alcohol | 0.1 to 0.5 |
| Purified water | q.s to 100 |

Manufacturing Procedure:

Flunisolide is dissolved in benzyl alcohol under stirring or heating up to 45° C.-50° C.

Citric acid and sodium citrate are dissolved in a mixture of purified water and propylene glycol and heated up to 60° C.-65° C. to constitute aqueous phase.

The oily phase components, i.e., a mixture of cetostearyl alcohol, cetomacrogol 1000, isopropyl myristate and dimethicone 350, are melted at 60° C.-65° C. and mixed well. The drug solution is added to the oily phase.

The oily phase containing the drug solution is added to aqueous phase under homogenisation for 20 to 30 minutes and cooled to room temperature under stirring.

Example 3: Topical Flunisolide Compositions

According to other specific embodiments, topical flunisolide compositions for delivery of flunisolide to the site of a skin infection or other skin condition on the skin can comprise:

TABLE 3

| Ingredient | % w/w |
|---|---|
| Flunisolide | 0.05 to 0.25 |
| Dimethyl isosorbide | 5 to 15 |
| Glyceryl stearate and PEG-100 stearate | 1 to 5 |
| Glyceryl monostearate | 1 to 5 |
| Purified water | 1 to 5 |
| Carbopol 980 | 0.1 to 1 |
| Citric acid | 0.05 to 1 |
| Diisopropanolamine | 0.001 to 0.01 |
| Propylene glycol | q.s to 100 |

Manufacturing Procedure:

Flunisolide is dissolved in dimethyl isosorbide under stirring or heating up to 45° C.-50° C.

Carbopol 980 is dissolved in a mixture of purified water and propylene glycol containing citric acid and heated up to 60° C.-65° C. to constitute the aqueous phase.

The oily phase components, i.e., a mixture of glyceryl monostearate, glyceryl stearate and PEG-100 stearate, are melted at 60° C.-65° C. and mixed well. The drug solution is added to the oily phase.

The oily phase containing drug solution is added to aqueous phase under homogenisation for 20 to 30 minutes. Diisopropanolamine is dissolved in the remaining quantity of propylene glycol and added to final emulsion. The final formulation is cooled to room temperature under stirring.

Example 4: Topical Flunisolide Compositions

According to other specific embodiments, topical flunisolide compositions for delivery of flunisolide to the site of a skin infection or other skin condition on the skin can comprise:

TABLE 4

| Ingredient | % w/w |
| --- | --- |
| Flunisolide | 0.05 to 0.25 |
| Cetyl alcohol | 1 to 10 |
| Diazolidinyl urea | 0.05 to 0.3 |
| Glycerin | 1 to 10 |
| Isopropyl isostearate | 1 to 5 |
| Isopropyl palmitate | 1 to 6 |
| Steareth-21 | 1 to 5 |
| Purified water | q.s to 100 |

Manufacturing Procedure:

Flunisolide is dissolved in isopropyl isostearate and isopropyl palmitate under stirring or heating up to 45° C.-50° C.

Diazolidinyl urea is dissolved in a mixture of purified water and glycerin and heated up to 60° C.-65° C. to constitute aqueous phase.

The oily phase, i.e., a mixture of cetyl alcohol and steareth 21, are melted at 60° C.-65° C. and mixed well. The drug solution is added to the oily phase.

The oily phase containing drug solution is added to the aqueous phase under homogenisation for 20 to 30 minutes and final formulation is cooled to room temperature under stirring.

Example 5: Topical Flunisolide Compositions

According to other specific embodiments, topical flunisolide compositions for delivery of flunisolide to the site of a skin infection or other skin condition on the skin can comprise:

TABLE 5

| Ingredient | % w/w |
| --- | --- |
| Flunisolide | 0.05 to 0.25 |
| Cetostearyl alcohol | 5 to 15 |
| Ceteareth 20 | 1 to 10 |
| Steareth 2 | 0.1 to 5 |
| Mineral oil | 1 to 10 |
| Pemulen TR-1 | 0.05 to 0.5 |
| Diethylene glycol monoethyl ether | 5 to 25 |
| Glycerin | 1 to 5 |
| Purified Water | q.s to 100 |

Manufacturing Procedure:

Glycerin is dissolved in part quantity of purified water. Pemulen TR-1 is dispersed in the remaining quantity of purified water and then added to the glycerin-water mixture and mixed well. This mixture is heated to 60° to 65° C. This constitutes the aqueous phase.

Cetostearyl alcohol, steareth 2, ceteareth 20, and mineral oil mixture are heated to 60° C. to 65° C. and melted completely. This constitutes the oil phase.

The oil phase is added to the aqueous phase and homogenized for 20 to 30 minutes. This constitutes the cream base. Flunisolide, when added, is dissolved in diethylene glycol monoethyl ether and added to the cream base, homogenized for 10 to 15 minutes and cooled to room temperature under stirring.

Example 6: Topical Flunisolide Composition

According to other specific embodiments, topical flunisolide compositions for delivery of flunisolide to the site of a skin infection or other skin condition on the skin can comprise:

TABLE 6

| Ingredient | % w/w |
| --- | --- |
| Flunisolide | 0.05 to 0.25 |
| Cetostearyl alcohol | 5 to 15 |
| Ceteareth 20 | 1 to 10 |
| Steareth 2 | 0.1 to 5 |
| Mineral oil | 1 to 10 |
| Dimethicone 350 | 0.5 to 5 |
| Pemulen TR-1 | 0.05 to 0.5 |
| Propylene Glycol | 5 to 25 |
| Methyl Paraben | 0.01 to 0.5 |
| Propyl paraben | 0.01 to 0.5 |
| Glycerin | 1 to 5 |
| Purified Water | q.s to 100 |

Manufacturing Procedure:

Glycerin and methyl paraben are dissolved in part quantity of purified water. Pemulen TR-1 is dispersed in the remaining quantity of purified water and then added to the glycerin and methyl paraben mixture and mixed well. This mixture is heated to 60° to 65° C. This constitutes the aqueous phase.

Cetostearyl alcohol, Steareth 2, ceteareth 20, mineral oil, dimethicone 350 and propyl paraben mixture are heated to 60° C. to 65° C. and melted completely. This constitutes the oil phase.

The oil phase is added to the aqueous phase and homogenized for 20 to 30 minutes. This constitutes the cream base. Flunisolide is dissolved in propylene glycol and added to the cream base and homogenized for 10 to 15 minutes. It is then cooled to room temperature under stirring.

Example 7: Topical Flunisolide Compositions

According to other specific embodiments, topical flunisolide compositions for delivery of flunisolide to the site of a skin infection or other skin condition on the skin can comprise:

TABLE 7

| Ingredient | % w/w |
| --- | --- |
| Flunisolide | 0.05 to 0.25 |
| Cetostearyl alcohol | 5 to 15 |
| Ceteareth 20 | 1 to 10 |
| Steareth 2 | 0.1 to 5 |
| Mineral oil | 1 to 10 |
| Dimethicone 350 | 0.5 to 5 |
| Pemulen TR-1 | 0.05 to 0.5 |
| Dimethyl isosorbide | 5 to 25 |
| Methyl Paraben | 0.01 to 0.5 |
| Propyl paraben | 0.01 to 0.5 |
| Glycerin | 1 to 5 |
| Purified Water | q.s to 100 |

Manufacturing Procedure:

Glycerin and methyl paraben are dissolved in part quantity of purified water. Pemulen TR-1 is dispersed in the remaining quantity of purified water and then added to the glycerin and methyl paraben mixture and mixed well. This mixture is heated to 60° to 65° C. This constitutes the aqueous phase.

Cetostearyl alcohol, Steareth 2, ceteareth 20, mineral oil, dimethicone 350 and propyl paraben mixture are heated to 60° C. to 65° C. and melted completely. This constitutes the oil phase.

The oil phase is added to the aqueous phase and homogenized for 20 to 30 minutes. This constitutes the cream base. Flunisolide is dissolved in dimethyl isosorbide and added to the cream base and homogenized for 10 to 15 minutes. It is then cooled to room temperature under stirring.

Example 8: Topical Flunisolide Compositions

According to other specific embodiments, topical flunisolide compositions for delivery of flunisolide to the site of a skin infection or other skin condition on the skin can comprise:

TABLE 8

| Ingredient | % w/w |
| --- | --- |
| Flunisolide | 0.05 to 0.25 |
| Cetostearyl alcohol | 5 to 15 |
| Ceteareth 20 | 1 to 10 |
| Steareth 2 | 0.1 to 5 |
| Mineral oil | 1 to 10 |
| Dimethicone 350 | 0.5 to 5 |
| Pemulen TR-1 | 0.05 to 0.5 |
| Dimethyl sulfoxide | 5 to 40 |
| Methyl Paraben | 0.01 to 0.5 |
| Propyl paraben | 0.01 to 0.5 |
| Glycerin | 1 to 5 |
| Purified Water | q.s to 100 |

Manufacturing Procedure:

Glycerin and methyl paraben are dissolved in part quantity of purified water. Pemulen TR-1 is dispersed in the remaining quantity of purified water and then added to glycerin and methyl paraben mixture and mixed well. This mixture is heated to 60° C. to 65° C. This constitutes the aqueous phase.

Cetostearyl alcohol, Steareth 2, ceteareth 20, mineral oil, dimethicone 350 and propyl paraben mixture is heated to 60° C. to 65° C. and melted completely. This constitutes the oil phase.

The oil phase is added to the aqueous phase and homogenized for 20 to 30 minutes. This constitutes the cream base. Flunisolide is dissolved in dimethyl sulfoxide and added to the cream base and homogenized for 10 to 15 minutes. It is then cooled to room temperature under stirring.

Example 9: Topical Flunisolide Compositions

According to other specific embodiments, topical flunisolide compositions for delivery of flunisolide to the site of a skin infection or other skin condition on the skin can comprise:

TABLE 9

| Ingredient | % w/w |
| --- | --- |
| Flunisolide | 0.05 to 0.25 |
| Cetostearyl alcohol | 5 to 15 |
| Ceteareth 20 | 1 to 10 |
| Steareth 2 | 0.1 to 5 |
| Mineral oil | 1 to 10 |
| Dimethicone 350 | 0.5 to 5 |
| Pemulen TR-1 | 0.05 to 0.5 |
| PEG 7 methyl ether | 5 to 25 |
| Methyl Paraben | 0.01 to 0.5 |
| Propyl paraben | 0.01 to 0.5 |
| Glycerin | 1 to 5 |
| Purified Water | q.s to 100 |

Manufacturing Procedure:

Glycerin and methyl paraben is dissolved in part quantity of purified water. Pemulen TR-1 is dispersed in the remaining quantity of purified water and then added to glycerin and methyl paraben mixture and mixed well. This mixture is heated to 60° to 65° C. This constitutes the aqueous phase.

Cetostearyl alcohol, Steareth 2, ceteareth 20, mineral oil, dimethicone 350 and propyl paraben mixture are heated to 60° C. to 65° C. and melted completely. This constitutes the oil phase.

The oil phase is added to the aqueous phase and homogenized for 20 to 30 minutes. This constitutes the cream base. Flunisolide is dissolved in PEG 7 methyl ether and added to the cream base and homogenized for 10 to 15 minutes. It is then cooled to room temperature under stirring.

Example 10: Topical Flunisolide Compositions

According to other specific embodiments, topical flunisolide compositions for delivery of flunisolide to the site of a skin infection or other skin condition on the skin can comprise:

TABLE 10

| Ingredient | % w/w |
| --- | --- |
| Flunisolide | 0.05 to 0.25 |
| Cetostearyl alcohol | 5 to 15 |
| Ceteareth 20 | 1 to 10 |
| Steareth 2 | 0.1 to 5 |
| Mineral oil | 1 to 10 |
| Dimethicone 350 | 0.5 to 5 |
| Pemulen TR-1 | 0.05 to 0.5 |
| Diethylene glycol monoethyl ether | 5-25 |
| Glycerin | 1 to 5 |
| Purified Water | q.s to 100 |

Manufacturing Procedure:

Glycerin is dissolved in part quantity of purified water. Pemulen TR-1 is dispersed in remaining quantity of purified water and then added to a glycerin-water mixture and mixed well. This mixture is heated to 60° to 65° C. This constitutes the aqueous phase.

Cetostearyl alcohol, Steareth 2, ceteareth 20, mineral oil, dimethicone 350 mixture is heated to 60° C. to 65° C. and melted completely. This constitutes the oil phase.

The oil phase is added to the aqueous phase and homogenized for 20 to 30 minutes. This constitutes the cream base. Flunisolide is dissolved in benzyl alcohol, added to the cream base and homogenized for 10 to 15 minutes. It is then cooled to room temperature under stirring.

Example 11: Topical Flunisolide Compositions

According to other specific embodiments, topical flunisolide compositions for delivery of flunisolide to the site of a skin infection or other skin condition on the skin can comprise:

TABLE 11

| Ingredient | % w/w |
|---|---|
| Flunisolide | 0.05 to 0.25 |
| Cetostearyl alcohol | 5 to 15 |
| Ceteareth 20 | 1 to 10 |
| Steareth 2 | 0.1 to 5 |
| Isopropyl myristate | 5 to 35 |
| Pemulen TR-1 | 0.05 to 0.5 |
| Benzyl alcohol | 0.5 to 5 |
| Glycerin | 1 to 5 |
| Purified Water | q.s to 100 |

Manufacturing Procedure:

Glycerin is dissolved in part quantity of purified water. Pemulen TR-1 is dispersed in remaining quantity of purified water and then added to a glycerin and water mixture and mixed well. This mixture is heated to 60° to 65° C. This constitutes the aqueous phase.

Cetostearyl alcohol, Steareth 2, ceteareth 20 mixture is heated to 60° C. to 65° C. and melted completely. This constitutes the oil phase.

Flunisolide is dissolved in the isopropyl myristate and benzyl alcohol mixture and added to the oil phase and mixed well. This constitutes the oil phase with the drug.

The oil phase with the drug is added to the aqueous phase and homogenized for 20 to 30 minutes. It is then cooled to room temperature under stirring.

Example 12: Topical Flunisolide Compositions

According to other specific embodiments, topical flunisolide compositions for delivery of flunisolide to the site of a skin infection or other skin condition on the skin comprise those set forth in Table 12, which is set forth below:

TABLE 12

| Emulsion Components | Ingredients (% w/w) | Anhydrous | | | | | | Hemihydrate | | |
|---|---|---|---|---|---|---|---|---|---|---|
| | | Example Nos. | | | | | | | | |
| | | 12A | 12B | 12C | 12D | 12E | 12F | 12G | 12H | 12I |
| Drug Phase | Flunisolide | 0.25 | 0.25 | 0.25 | 0.1 | 0.25 | 0.1 | 0.1 | 0.25 | 0.1 |
| | Benzyl alcohol | 1.0 | 2.0 | 2.0 | 2.0 | 2.0 | 2.0 | 2.0 | 2.0 | 2.0 |
| Oil Phase | Cetostearyl alcohol | 12.0 | 10.0 | 12.0 | 12.0 | 12.0 | 12.0 | 12.0 | 12.0 | 12.0 |
| | Stearyl alcohol | 1.5 | 1.5 | — | — | — | — | — | — | — |
| | Oleic acid | 1.5 | 1.5 | — | — | — | — | — | — | — |
| | Cetyl esters wax | — | — | 3.0 | 3.0 | 3.0 | 3.0 | 3.0 | 3.0 | 3.0 |
| | Octyldodecanol | 12.0 | 13.5 | 12.0 | 12.0 | 12.0 | 12.0 | 12.0 | 12.0 | 12.0 |
| | Sorbitan monostearate | 2.4 | 2.0 | 2.4 | 2.4 | 2.4 | 2.4 | 2.4 | 2.4 | 2.4 |
| | Polysorbate 60 | 0.6 | 1.5 | 0.6 | 0.6 | 0.6 | 0.6 | 0.6 | 0.6 | 0.6 |
| | Butylatedhydroxytoluene (BHT) | — | — | — | — | 0.1 | 0.1 | — | — | 0.1 |
| Aqueous Phase | Disodium edetate | — | — | — | — | 0.05 | 0.05 | — | — | 0.05 |
| | Purified water | q.s. to 100 | q.s. to 100 | q.s. to 100 | q.s. to 100 | q.s. to 100 | q.s. to 100 | q.s. to 100 | q.s. to 100 | q.s. to 100 |

Stability Data for Flunisolide Compositions of Table 12

Formulation 12C:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | 0.08 | 0.35 | 0.05 | 0.03 | 0.02 | 0.18 | ND | 0.09 | ND | 0.01 | 0.86 | 99.6 |
| 1M-25° C./60% RH | 0.01 | 0.29 | 0.04 | 0.02 | 0.02 | 0.15 | ND | 0.07 | ND | 0.03 | 0.68 | 99.9 |
| 2M-25° C./60% RH | 0.05 | 0.33 | 0.05 | 0.03 | 0.03 | 0.17 | ND | 0.08 | ND | 0.02 | 0.76 | 99.8 |
| 3M-25° C./60% RH | 0.11 | 0.29 | 0.04 | 0.03 | 0.03 | 0.19 | ND | 0.06 | ND | ND | 0.75 | 99.8 |
| 1M-30° C./65% RH | 0.02 | 0.26 | 0.04 | 0.02 | 0.02 | 0.14 | ND | 0.06 | ND | 0.02 | 0.62 | 98.9 |
| 2M-30° C./65% RH | 0.08 | 0.33 | 0.05 | 0.03 | 0.04 | 0.17 | ND | 0.07 | ND | 0.04 | 0.81 | 98.9 |
| 3M-30° C./65% RH | 0.13 | 0.3 | 0.04 | ND | ND | 0.2 | ND | 0.08 | ND | 0.04 | 0.79 | 101.9 |
| 1M-40° C./75% RH | 0.03 | 0.28 | 0.04 | 0.02 | 0.03 | 0.15 | ND | 0.05 | ND | 0.06 | 0.72 | 98.2 |
| 2M-40° C./75% RH | 0.16 | 0.31 | 0.05 | 0.03 | 0.04 | 0.22 | ND | 0.05 | ND | 0.05 | 0.91 | 100.5 |
| 3M-40° C./75% RH | 0.26 | 0.3 | 0.05 | ND | 0.04 | 0.18 | ND | 0.05 | ND | 0.07 | 0.95 | 103.0 |

Formulation 12D:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | 0.04 | 0.24 | 0.04 | 0.02 | 0.02 | 0.17 | ND | 0.01 | ND | 0.01 | 0.57 | 99.0 |
| 1M-25° C./60% RH | 0.20 | 0.28 | 0.04 | 0.03 | 0.03 | 0.22 | ND | ND | ND | 0.01 | 0.81 | 97.1 |
| 2M-25° C./60% RH | 0.12 | 0.26 | 0.05 | ND | ND | 0.16 | ND | ND | ND | 0.03 | 0.62 | 98.3 |
| 3M-25° C./60% RH | 0.19 | 0.27 | 0.04 | 0.02 | 0.07 | 0.2 | ND | ND | ND | 0.07 | 0.87 | 104.4 |
| 1M-30° C./65% RH | 0.20 | 0.28 | 0.04 | 0.03 | 0.03 | 0.2 | ND | ND | ND | 0.14 | 1.04 | 98.1 |
| 2M-30° C./65% RH | 0.15 | 0.28 | ND | ND | 0.04 | 0.2 | ND | ND | ND | 0.05 | 0.74 | 98.1 |
| 3M-30° C./65% RH | 0.18 | 0.27 | 0.04 | ND | 0.16 | 0.21 | ND | 0.02 | ND | 0.16 | 1.04 | 101.8 |
| 1M-40° C./75% RH | 0.20 | 0.28 | 0.04 | 0.03 | 0.07 | 0.19 | ND | ND | ND | 0.05 | 0.94 | 99.4 |
| 2M-40° C./75% RH | 0.32 | 0.28 | 0.05 | ND | 0.08 | 0.22 | ND | ND | ND | 0.05 | 1.0 | 97.4 |
| 3M-40° C./75% RH | 0.42 | 0.28 | 0.04 | ND | 0.12 | 0.21 | ND | 0.04 | ND | 0.11 | 1.22 | 103.9 |

Formulation 12E:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | 0.04 | 0.29 | 0.05 | ND | 0.03 | ND | ND | 0.17 | ND | ND | 0.58 | 100.0 |
| 1M-25° C./60% RH | 0.04 | 0.32 | 0.05 | 0.03 | 0.03 | 0.05 | ND | 0.18 | ND | ND | 0.7 | 99.4 |
| 2M-25° C./60% RH | 0.04 | 0.31 | ND | ND | ND | 0.05 | ND | 0.13 | ND | ND | 0.53 | 95.3 |
| 3M-25° C./60% RH | 0.05 | 0.30 | 0.04 | ND | 0.02 | ND | ND | 0.11 | ND | 0.01 | 0.53 | 102.3 |
| 1M-30° C./65% RH | 0.04 | 0.31 | 0.04 | 0.03 | 0.02 | 0.04 | ND | 0.18 | ND | ND | 0.66 | 97.6 |
| 2M-30° C./65% RH | ND | 0.29 | 0.04 | ND | 0.01 | 0.03 | ND | 0.13 | ND | ND | 0.50 | 95.5 |
| 3M-30° C./65% RH | 0.06 | 0.3 | 0.04 | ND | 0.02 | ND | ND | 0.12 | ND | 0.10 | 0.55 | 103.2 |
| 1M-40° C./75% RH | 0.08 | 0.29 | 0.04 | 0.02 | 0.03 | 0.08 | ND | 0.14 | ND | ND | 0.68 | 94.5 |
| 2M-40° C./75% RH | 0.10 | 0.26 | 0.03 | ND | 0.02 | 0.09 | ND | 0.08 | ND | ND | 0.58 | 102.4 |
| 3M-40° C./75% RH | 0.12 | 0.28 | 0.03 | ND | ND | ND | ND | 0.06 | ND | 0.03 | 0.52 | 104.4 |

Formulation 12F:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| 1M-25° C./60% RH | 0.03 | 0.27 | 0.04 | 0.02 | 0.06 | 0.04 | 0 | 0.16 | 0 | 0.01 | 0.63 | 102.7 |
| 2M-25° C./60% RH | 0.13 | 0.26 | 0.03 | ND | 0.02 | 0.06 | ND | 0.1 | ND | ND | 0.6 | 100.1 |
| 3M-25° C./60% RH | 0.02 | 0.26 | 0.04 | 0.04 | 0.02 | 0.05 | ND | 0.15 | ND | 0.02 | 0.6 | 104.2 |
| 1M-30° C./65% RH | 0.03 | 0.27 | 0.04 | 0 | 0.02 | 0.06 | 0 | 0.15 | 0 | 0 | 0.57 | 103.7 |
| 2M-30° C./65% RH | 0.12 | 0.26 | 0.04 | ND | 0.02 | 0.07 | ND | 0.1 | ND | 0.01 | 0.63 | 99.0 |
| 3M-30° C./65% RH | 0.03 | 0.26 | 0.04 | 0.03 | 0.02 | 0.06 | ND | 0.14 | ND | 0.01 | 0.59 | 100.0 |
| 1M-40° C./75% RH | 0.06 | 0.26 | 0.04 | 0 | 0.02 | 0.07 | 0 | 0.12 | 0 | 0.01 | 0.58 | 103.6 |
| 2M-40° C./75% RH | 0.16 | 0.26 | 0.04 | ND | 0.02 | 0.1 | ND | 0.07 | ND | 0.02 | 0.69 | 100.2 |

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| 3M-40° C./75% RH | 0.08 | 0.24 | 0.04 | 0.03 | 0.02 | 0.1 | ND | 0.08 | ND | 0.04 | 0.63 | 98.5 |

Formulation 12G:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | 0.04 | 0.03 | 0.02 | ND | 0.02 | ND | ND | ND | ND | ND | 0.11 | 96.6 |
| 1M-25° C./60% RH | 0.07 | 0.04 | 0.02 | ND | 0.05 | 0.02 | ND | ND | ND | 0.02 | 0.23 | 96.5 |
| 2M-25° C./60% RH | 0.08 | ND | 0.04 | ND | 0.04 | ND | ND | ND | ND | 0.03 | 0.21 | 94.0 |
| 3M-25° C./60% RH | 0.06 | 0.05 | 0.03 | ND | 0.07 | ND | ND | ND | ND | 0.03 | 0.26 | 92.7 |
| 1M-30° C./65% RH | 0.07 | 0.04 | 0.02 | ND | 0.05 | 0.02 | ND | ND | ND | 0.02 | 0.23 | 95.4 |
| 2M-30° C./65% RH | 0.05 | ND | 0.04 | ND | 0.03 | ND | ND | ND | ND | 0.03 | 0.16 | 95.5 |
| 3M-30° C./65% RH | 0.07 | 0.04 | 0.02 | ND | 0.08 | ND | ND | ND | ND | 0.07 | 0.39 | 89.5 |
| 1M-40° C./75% RH | 0.14 | 0.04 | 0.02 | ND | 0.05 | 0.02 | ND | ND | ND | 0.03 | 0.33 | 95.3 |
| 2M-40° C./75% RH | 0.14 | ND | 0.04 | ND | 0.04 | ND | ND | ND | ND | 0.02 | 0.24 | 93.8 |
| 3M-40° C./75% RH | 0.06 | 0.04 | 0.03 | ND | 0.12 | ND | ND | ND | ND | 0.07 | 0.43 | 92.0 |

Formulation 12H:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | 0.18 | 0.04 | 0.02 | ND | ND | ND | ND | ND | ND | ND | 0.24 | 100.5 |
| 1M-25° C./60% RH | 0.16 | 0.04 | 0.02 | ND | ND | ND | ND | ND | ND | 0.02 | 0.32 | 99.6 |
| 2M-25° C./60% RH | 0.21 | 0.06 | 0.02 | ND | 0.04 | ND | ND | ND | ND | 0.03 | 0.36 | 99.6 |
| 3M-25° C./60% RH | 0.15 | 0.04 | 0.03 | ND | 0.06 | ND | 0.04 | ND | 0.11 | 0.52 | 97.0 |
| 1M-30° C./65% RH | 0.17 | 0.04 | 0.02 | 0.01 | 0.05 | 0.03 | ND | ND | ND | 0.03 | 0.36 | 100.7 |
| 2M-30° C./65% RH | 0.21 | 0.07 | 0.05 | ND | 0.05 | ND | ND | ND | ND | 0.02 | 0.4 | 102.4 |
| 3M-30° C./65% RH | 0.16 | 0.05 | 0.03 | ND | 0.07 | ND | ND | 0.02 | ND | 0.09 | 0.5 | 96.15 |
| 1M-40° C./75% RH | 0.23 | 0.04 | 0.02 | 0.01 | 0.05 | 0.03 | ND | ND | ND | 0.03 | 0.43 | 97.8 |
| 2M-40° C./75% RH | 0.17 | 0.12 | ND | ND | 0.05 | ND | ND | ND | ND | 0.02 | 0.36 | 99.1 |
| 3M-40° C./75% RH | 0.29 | 0.04 | 0.04 | ND | 0.08 | ND | ND | 0.04 | ND | 0.09 | 0.69 | 97.9 |

Formulation 12I:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | ND | 0.06 | 0.04 | ND | 0.05 | ND | ND | ND | ND | ND | 0.15 | 99.3 |
| 1M-25° C./60% RH | 0.02 | 0.04 | 0.02 | 0 | 0.03 | 0 | 0 | 0 | 0 | 0.01 | 0.12 | 105.2 |
| 2M-25° C./60% RH | 0.11 | 0.04 | 0.02 | ND | 0.04 | 0.02 | ND | ND | ND | 0.02 | 0.26 | 102.1 |
| 3M-25° C./60% RH | 0.03 | 0.03 | 0.02 | 0.02 | 0.04 | ND | ND | ND | ND | 0.01 | 0.15 | 102.2 |
| 1M-30° C./65% RH | 0.03 | 0.04 | 0.02 | 0 | 0.04 | 0 | 0 | 0 | 0 | 0.01 | 0.14 | 104.0 |

-continued

| Condition | 21-Aldehyde | Desonide | Flunisolide Imp-A | Fluran-drenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| 2M-30° C./65% RH | 0.11 | 0.04 | 0.02 | ND | 0.04 | 0.02 | ND | ND | ND | 0.02 | 0.26 | 103.4 |
| 3M-30° C./65% RH | 0.04 | 0.03 | 0.02 | 0.01 | 0.05 | ND | ND | ND | ND | 0.02 | 0.17 | 102.6 |
| 1M-40° C./75% RH | 0.06 | 0.04 | 0.02 | 0 | 0.04 | 0 | 0 | 0 | 0 | 0.02 | 0.18 | 105.2 |
| 2M-40° C./75% RH | 0.14 | 0.04 | 0.02 | ND | 0.04 | 0.02 | ND | ND | ND | 0.03 | 0.31 | 100.1 |
| 3M-40° C./75% RH | 0.09 | 0.04 | 0.03 | 0.02 | 0.05 | ND | ND | ND | ND | 0.04 | 0.27 | 101.9 |

Manufacturing Procedure:

The components of the oil phase were taken in a stainless steel container and heated to a temperature between 65 to 70° C. The drug phase was prepared by dissolving flunisolide (either the anhydrous form or the hemihydrate form) in benzyl alcohol at 65° C., followed by sonication for 20 minutes. The oil phase was mixed with the drug phase.

The components of the aqueous phase were taken in a stainless steel container and heated to a temperature between 65 to 70° C. The oil phase containing the drug phase was added to the aqueous phase under homogenization for 20 minutes to obtain an emulsion. The emulsion was cooled to room temperature (25° C.) under stirring.

Example 13: Topical Flunisolide Compositions

According to other specific embodiments, topical flunisolide compositions for delivery of flunisolide to the site of a skin infection or other skin condition on the skin comprise those set forth in Table 13, which is set forth below:

TABLE 13

| Emulsion Components | Ingredients (% w/w) | Anhydrous | | | Hemihydrate |
|---|---|---|---|---|---|
| | | Example Nos. | | | |
| | | 13A | 13B | 13C | 13D |
| Drug Phase | Flunisolide | 0.25 | 0.25 | 0.1 | 0.1 |
| | Benzyl Alcohol | 2.0 | 2.0 | 2.0 | 2.0 |
| Oil Phase | Cetostearyl alcohol | 12.0 | 12.0 | 12.0 | 12.0 |
| | Cetyl esters wax | 3.0 | 3.0 | 3.0 | 3.0 |
| | Isopropyl Myristate | 10.0 | 10.0 | 10.0 | 10.0 |
| | Octyldodecanol | 13.5 | 12.0 | 12.0 | 12.0 |
| | Sorbitan monostearate | 2.4 | 2.4 | 2.4 | 2.4 |
| | Polysorbate 60 | 0.6 | 0.6 | 0.6 | 0.6 |
| | Butylatedhydroxy-toluene (BHT) | — | 0.1 | 0.1 | 0.1 |
| Aqueous Phase | Disodium edetate | — | 0.05 | 0.05 | 0.05 |
| | Purified water | q.s. to 100 | q.s. to 100 | q.s. to 100 | q.s. to 100 |

Stability Data for Table 13

Formulation 13A:

| Condition | 21-Aldehyde | Desonide | Flunisolide Imp-A | Fluran-drenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | 0.04 | 0.31 | 0.04 | 0.02 | 0.02 | 0.10 | ND | 0.15 | ND | ND | 0.70 | 99.6 |
| 1M-25° C./60% RH | 0.01 | 0.27 | 0.04 | 0.02 | 0.02 | 0.08 | ND | 0.11 | ND | 0.02 | 0.61 | 97.3 |
| 2M-25° C./60% RH | 0.08 | 0.32 | 0.05 | 0.03 | 0.05 | 0.17 | ND | 0.14 | ND | 0.01 | 0.80 | 100.3 |
| 3M-25° C./60% RH | 0.07 | 0.28 | 0.06 | ND | ND | ND | ND | 0.13 | ND | 0.01 | 0.55 | 98 |
| 1M-30° C./65% RH | ND | 0.28 | 0.04 | 0.03 | 0.03 | 0.13 | ND | 0.12 | ND | 0.03 | 0.68 | 98.6 |
| 2M-30° C./65% RH | 0.08 | 0.3 | 0.05 | 0.03 | 0.03 | 0.15 | ND | 0.12 | ND | 0.01 | 0.74 | 95.8 |
| 3M-30° C./65% RH | 0.10 | 0.29 | 0.05 | ND | ND | 0.11 | ND | 0.12 | ND | ND | 0.67 | 99.6 |
| 1M-40° C./75% RH | 0.01 | 0.25 | 0.03 | 0.02 | 0.03 | 0.15 | ND | 0.04 | ND | 0.08 | 0.65 | 81.3 |
| 2M-40° C./75% RH | 0.28 | 0.32 | 0.05 | 0.04 | 0.04 | 0.25 | ND | 0.05 | ND | 0.03 | 1.01 | 89.2 |
| 3M-40° C./75% RH | 0.3 | 0.26 | 0.05 | ND | ND | 0.17 | ND | 0.04 | ND | 0.06 | 0.88 | 84.5 |

Formulation 13B:

| Condition | 21-Aldehyde | Desonide | Flunisolide Imp-A | Fluran-drenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | ND | 0.29 | 0.04 | ND | 0.04 | ND | ND | 0.18 | ND | ND | 0.55 | 99.9 |
| 1M-25° C./60% RH | 0.03 | 0.35 | 0.05 | 0.04 | 0.02 | 0.05 | ND | 0.20 | ND | 0.01 | 0.75 | 100.4 |
| 2M-25° C./60% RH | 0.03 | 0.30 | 0.04 | 0.03 | ND | 0.05 | ND | 0.14 | ND | ND | 0.59 | 102.4 |

-continued

Formulation 13B (continued):

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| 3M-25° C./60% RH | 0.08 | 0.31 | 0.05 | ND | 0.02 | 0.06 | ND | 0.2 | ND | 0.01 | 0.73 | 104.0 |
| 1M-30° C./65% RH | 0.04 | 0.29 | 0.04 | 0.02 | 0.01 | 0.03 | ND | 0.18 | ND | 0.01 | 0.62 | 105.7 |
| 2M-30° C./65% RH | 0.03 | 0.31 | 0.05 | 0.09 | ND | 0.05 | ND | 0.15 | ND | ND | 0.68 | 104.8 |
| 3M-30° C./65% RH | 0.06 | 0.32 | 0.05 | ND | 0.01 | 0.06 | ND | 0.16 | ND | 0.02 | 0.69 | 94.8 |
| 1M-40° C./75% RH | 0.05 | 0.29 | 0.04 | 0.04 | 0.01 | 0.06 | ND | 0.15 | ND | 0.01 | 0.65 | 97.4 |
| 2M-40° C./75% RH | 0.07 | 0.31 | 0.05 | 0.08 | ND | 0.10 | ND | 0.11 | ND | ND | 0.72 | 113.2 |
| 3M-40° C./75% RH | 0.1 | 0.31 | 0.05 | 0.03 | 0.05 | 0.10 | ND | 0.14 | ND | 0.02 | 0.83 | 107.1 |

Formulation 13C:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | ND | 0.29 | 0.07 | 0.01 | 0.02 | ND | ND | 0.18 | ND | ND | 0.57 | 97.7 |
| 1M-25° C./60% RH | 0.02 | 0.3 | 0.04 | 0.02 | 0.03 | 0.04 | 0 | 0.17 | 0 | 0.01 | 0.63 | 102.3 |
| 2M-25° C./60% RH | 0.09 | 0.28 | 0.04 | ND | 0.02 | 0.05 | ND | 0.14 | ND | 0.02 | 0.65 | 99.5 |
| 3M-25° C./60% RH | 0.02 | 0.28 | 0.03 | 0.04 | 0.03 | 0.05 | ND | 0.16 | ND | ND | 0.61 | 99.4 |
| 1M-30° C./65% RH | 0.02 | 0.29 | 0.05 | 0.03 | 0.02 | 0.04 | 0 | 0.17 | 0 | 0.01 | 0.63 | 102.5 |
| 2M-30° C./65% RH | 0.07 | 0.29 | 0.04 | ND | 0.03 | 0.07 | ND | 0.14 | ND | 0.02 | 0.67 | 112.7 |
| 3M-30° C./65% RH | 0.02 | 0.25 | 0.04 | 0.03 | 0.03 | 0.05 | ND | 0.15 | ND | 0.01 | 0.58 | 99.8 |
| 1M-40° C./75% RH | 0.04 | 0.3 | 0.05 | 0.03 | 0.02 | 0.07 | 0 | 0.15 | 0 | 0.01 | 0.67 | 109.4 |
| 2M-40° C./75% RH | 0.13 | 0.28 | 0.05 | ND | 0.03 | 0.09 | ND | 0.14 | ND | 0.02 | 0.73 | 102.6 |
| 3M-40° C./75% RH | 0.05 | 0.26 | 0.05 | 0.04 | 0.03 | 0.09 | ND | 0.1 | ND | 0.01 | 0.63 | 100.6 |

Formulation 13D:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | 0.03 | 0.27 | 0.06 | ND | 0.06 | ND | ND | ND | ND | 0.13 | 0.74 | 96.7 |
| 1M-25° C./60% RH | 0.03 | 0.27 | 0.04 | 0 | 0.06 | 0 | 0 | 0 | 0 | 0.03 | 0.45 | 101.8 |
| 2M-25° C./60% RH | 0.10 | 0.27 | 0.04 | ND | 0.06 | 0.02 | ND | ND | ND | 0.05 | 0.56 | 99.2 |
| 3M-25° C./60% RH | 0.02 | 0.22 | 0.04 | ND | 0.06 | ND | ND | ND | ND | 0.04 | 0.45 | 97.8 |
| 1M-30° C./65% RH | 0.03 | 0.27 | 0.04 | 0 | 0.06 | 0 | 0 | 0 | 0 | 0.04 | 0.46 | 101.4 |
| 2M-30° C./65% RH | 0.11 | 0.27 | 0.04 | ND | 0.07 | 0.02 | ND | ND | ND | 0.05 | 0.58 | 98.6 |
| 3M-30° C./65% RH | 0.03 | 0.23 | 0.04 | 0.02 | 0.05 | ND | ND | ND | ND | 0.05 | 0.49 | 99.7 |
| 1M-40° C./75% RH | 0.04 | 0.25 | 0.03 | 0 | 0.06 | 0 | 0 | 0 | 0 | 0.03 | 0.43 | 94.3 |
| 2M-40° C./75% RH | 0.13 | 0.28 | 0.04 | ND | 0.07 | 0.02 | ND | ND | ND | 0.07 | 0.64 | 101.3 |
| 3M-40° C./75% RH | 0.08 | 0.25 | 0.04 | 0.02 | 0.05 | ND | ND | ND | ND | 0.07 | 0.58 | 98.5 |

Manufacturing Procedure:

The components of the oil phase were taken in a stainless steel container and heated to a temperature between 65 to 70° C. The drug phase was prepared by dissolving flunisolide (either the anhydrous form or the hemihydrate form) in benzyl alcohol at 65° C., followed by sonication for 20 minutes. The oil phase was mixed with the drug phase.

The components of aqueous phase were taken in suitable stainless steel container and heated to temperature between 65 to 70° C. The oil phase containing the drug phase was added to the aqueous phase under homogenization for 20 minutes to obtain an emulsion.

The emulsion was cooled to room temperature (25° C.) under stirring.

Example 14: Topical Flunisolide Composition

According to other specific embodiments, topical flunisolide compositions for delivery of flunisolide to the site of a skin infection or other skin condition on the skin comprise those set forth in Table 14, which is set forth below:

TABLE 14

| Emulsion Components | Ingredients (% w/w) | Anhydrous | | Hemihydrate | |
|---|---|---|---|---|---|
| | | Example Nos. | | | |
| | | 14A | 14B | 14C | 14D |
| Drug Phase | Flunisolide | 0.25 | 0.25 | 0.1 | 0.1 |
| | Benzyl Alcohol | 2.0 | 2.0 | 2.0 | 2.0 |
| Oil Phase | Cetostearyl alcohol | 12.0 | 12.0 | 12.0 | 12.0 |
| | Cetyl esters wax | 3.0 | 3.0 | 3.0 | 3.0 |
| | Isopropyl Myristate | 12.0 | 12.0 | 12.0 | 12.0 |
| | Sorbitan monostearate | 2.4 | 2.4 | 2.4 | 2.4 |
| | Polysorbate 60 | 0.6 | 0.6 | 0.6 | 0.6 |
| | Butylatedhydroxytoluene (BHT) | — | 2.0 | 2.0 | 2.0 |
| Aqueous Phase | Disodium edetate | — | 0.1 | 0.1 | 0.1 |
| | Purified water | q.s. to 100 | q.s. to 100 | q.s. to 100 | q.s. to 100 |

Stability Data for Table 14

Formulation 14B:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Imp | Assay (%) |
|---|---|---|---|---|---|---|---|---|---|---|---|---|
| Initial | 0.16 | 0.29 | 0.05 | ND | ND | 0.09 | ND | 0.19 | ND | ND | 0.78 | 100.2 |
| 1M-25° C./60% RH | 0.18 | 0.3 | 0.05 | 0.08 | 0.02 | 0.05 | ND | 0.18 | ND | ND | 0.86 | 98.0 |
| 2M-25° C./60% RH | 0.17 | 0.28 | 0.05 | 0.08 | 0.02 | 0.05 | ND | 0.14 | ND | ND | 0.74 | 99.9 |
| 3M-25° C./60% RH | 0.19 | 0.3 | 0.04 | ND | 0.01 | 0.08 | ND | 0.12 | ND | 0.01 | 0.75 | 99.0 |
| 1M-30° C./65% RH | 0.18 | 0.03 | 0.04 | 0.12 | 0.02 | 0.05 | ND | 0.17 | ND | ND | 0.88 | 97.8 |
| 2M-30° C./65% RH | 0.16 | 0.26 | 0.04 | 0.07 | 0.02 | 0.05 | ND | 0.13 | ND | ND | 0.66 | 99.7 |
| 3M-30° C./65% RH | 0.20 | 0.30 | 0.04 | ND | 0.05 | 0.10 | ND | 0.11 | ND | 0.01 | 0.81 | 98.0 |
| 1M-40° C./75% RH | 0.20 | 0.3 | 0.05 | 0.11 | 0.02 | 0.06 | ND | 0.16 | ND | ND | 0.90 | 97.7 |
| 2M-40° C./75% RH | 0.22 | 0.27 | 0.05 | 0.08 | 0.02 | 0.07 | ND | 0.11 | ND | ND | 0.74 | 100.2 |
| 3M-40° C./75% RH | 0.29 | 0.31 | 0.04 | 0.06 | 0.04 | 0.07 | ND | 0.13 | ND | 0.05 | 0.99 | 98.2 |

Formulation 14C:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | 0.05 | 0.05 | ND | ND | 0.05 | ND | ND | ND | ND | ND | 0.15 | 98.6 |
| 1M-25° C./60% RH | 0.06 | 0.04 | 0.02 | 0 | 0.04 | ND | ND | ND | ND | 0.01 | 0.17 | 102.4 |
| 2M-25° C./60% RH | 0.13 | 0.04 | 0.02 | ND | 0.05 | 0.03 | ND | ND | ND | 0.01 | 0.28 | 97.7 |
| 3M-25° C./60% RH | 0.05 | 0.04 | 0.02 | ND | 0.06 | ND | ND | ND | ND | 0.01 | 0.18 | 99.9 |
| 1M-30° C./65% RH | 0.06 | 0.04 | 0.02 | 0 | 0.04 | 0 | 0 | 0 | 0 | 0.01 | 0.17 | 102.6 |
| 2M-30° C./65% RH | 0.14 | 0.04 | 0.03 | ND | 0.05 | 0.03 | ND | ND | ND | 0.02 | 0.33 | 96.9 |
| 3M-30° C./65% RH | 0.08 | 0.04 | 0.03 | ND | 0.05 | ND | ND | ND | ND | 0.02 | 0.22 | 100.3 |
| 1M-40° C./75% RH | 0.09 | 0.04 | 0.02 | 0 | 0.04 | 0 | 0 | 0 | 0 | 0.02 | 0.21 | 108.8 |
| 2M-40° C./75% RH | 0.17 | 0.04 | 0.02 | ND | 0.05 | 0.02 | ND | ND | ND | 0.04 | 0.36 | 100.6 |
| 3M-40° C./75% RH | 0.14 | 0.03 | 0.02 | ND | 0.05 | ND | ND | ND | ND | 0.03 | 0.27 | 99.1 |

Formulation 14D:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | 0.04 | 0.27 | 0.04 | ND | 0.05 | 0.07 | ND | 0.16 | ND | ND | 0.63 | 97.3 |
| 1M-25° C./60% RH | 0.05 | 0.27 | 0.05 | 0.02 | 0 | 0.04 | 0 | 0.16 | 0 | 0.01 | 0.6 | 99 |
| 2M-25° C./60% RH | 0.13 | 0.28 | 0.04 | ND | 0.02 | 0.06 | ND | 0.16 | ND | 0.02 | 0.71 | 100 |
| 3M-25° C./60% RH | 0.05 | 0.25 | 0.05 | 0.03 | 0.02 | 0.05 | ND | ND | ND | ND | 0.61 | 99.3 |
| 1M-30° C./65% RH | 0.06 | 0.27 | 0.04 | 0 | 0.02 | 0.04 | 0 | 0.15 | 0 | 0.01 | 0.59 | 106.6 |
| 2M-30° C./65% RH | 0.14 | 0.27 | 0.05 | ND | 0.02 | 0.06 | ND | 0.12 | ND | 0.02 | 0.68 | 97.8 |
| 3M-30° C./65% RH | 0.06 | 0.24 | 0.04 | 0.03 | 0.02 | 0.04 | ND | ND | ND | ND | 0.57 | 103 |
| 1M-40° C./75% RH | 0.09 | 0.26 | 0.04 | 0 | 0.02 | 0 | ND | 0 | 0 | 0.01 | 0.53 | 93.1 |
| 2M-40° C./75% RH | 0.17 | 0.28 | 0.05 | ND | 0.02 | 0.08 | ND | 0.08 | ND | 0.02 | 0.73 | 103.0 |
| 3M-40° C./75% RH | 0.14 | 0.23 | 0.05 | 0.04 | 0.03 | 0.07 | ND | ND | ND | 0.03 | 0.69 | 96.3 |

Manufacturing Procedure:

The components of the oil phase were taken in a stainless steel container and heated to a temperature between 65 to 70° C. The drug phase was prepared by dissolving flunisolide (either the anhydrous form or the hemihydrate form) in benzyl alcohol at 65° C., followed by sonication for 20 minutes. The oil phase was mixed with the drug phase. The components of aqueous phase were taken in a stainless steel container and heated to a temperature between 65 to 70° C. The oil phase containing the drug phase was added to the aqueous phase under homogenization for 20 minutes to obtain an emulsion. The emulsion was cooled to room temperature (25° C.) under stirring.

Example 15: Topical Flunisolide Composition

According to other specific embodiments, topical flunisolide compositions for delivery of flunisolide to the site of a skin infection or other skin condition on the skin comprise those set forth in Table 15, which is set forth below:

TABLE 15

| Emulsion Components | Ingredients (% w/w) | Anhydrous | | | Hemihydrate | |
|---|---|---|---|---|---|---|
| | | Example Nos. | | | | |
| | | 15A | 15B | 15C | 15D | 15E |
| Drug Phase | Flunisolide | 0.25 | 0.25 | 0.1 | 0.1 | 0.25 |
| | Benzyl Alcohol | 4.0 | 4.0 | 4.0 | 4.0 | 4.0 |
| Oil Phase | Medium Chain Triglyceride (MCT) | 15.0 | 15.0 | 12.0. | 12.0 | 12.0 |
| | Cetyl alcohol | 5.75 | 5.75 | 3.0 | 3.0 | 3.0 |
| | Stearyl alcohol | 8.1 | 8.1 | 4.0 | 4.0 | 4.0 |
| | White petrolatum | 8.1 | 8.1 | 4.0 | 4.0 | 4.0 |
| | Polysorbate 60 | 3.4 | 3.4 | 3.4 | 3.4 | 3.4 |
| | Sorbitan monostearate | 0.6 | 0.6 | 0.6 | 0.6 | 0.6 |
| | Butylatedhydroxytoluene (BHT) | 0.5 | 0.5 | 0.5 | 0.5 | 0.5 |
| Aqueous Phase | Glycerin | 2.0 | 2.0 | 2.0 | 2.0 | 2.0 |
| | Xanthan gum | 0.5 | 0.5 | 0.5 | 0.5 | 0.5 |
| | Sepineo P 600 | — | — | 2.0 | 2.0 | 2.0 |
| | Disodium edetate | 0.05 | 0.1 | 0.1 | 0.1 | 0.1 |
| | Purified water | q.s. to 100 | q.s. to 100 | q.s. to 100 | q.s. to 100 | q.s. to 100 |

Stability Data for Table 15

Formulation 15B:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Imp | Assay (%) |
|---|---|---|---|---|---|---|---|---|---|---|---|---|
| Initial | 0.04 | 0.29 | 0.05 | ND | ND | ND | ND | 0.17 | ND | ND | 0.55 | 98.2 |
| 1M-25° C./60% RH | 0.04 | 0.3 | 0.04 | 0.03 | 0.02 | 0.04 | ND | 0.19 | ND | 0.01 | 0.67 | 99.4 |
| 2M-25° C./60% RH | 0.03 | 0.28 | 0.04 | ND | ND | 0.04 | ND | 0.12 | ND | ND | 0.51 | 100.6 |
| 3M-25° C./60% RH | 0.11 | 0.3 | 0.04 | ND | 0.02 | 0.04 | ND | 0.18 | ND | 0.02 | 0.71 | 101.7 |
| 1M-30° C./65% RH | 0.04 | 0.33 | 0.05 | 0.03 | 0.02 | 0.05 | ND | 0.19 | ND | ND | 0.71 | 99.7 |
| 2M-30° C./65% RH | 0.04 | 0.29 | 0.04 | ND | ND | 0.05 | ND | 0.12 | ND | ND | 0.54 | 101.1 |
| 3M-30° C./65% RH | 0.07 | 0.29 | 0.04 | ND | 0.01 | 0.06 | ND | 0.16 | ND | ND | 0.63 | 99.8 |
| 1M-40° C./75% RH | 0.07 | 0.31 | 0.05 | 0.02 | 0.02 | 0.05 | ND | 0.17 | ND | ND | 0.69 | 101.2 |
| 2M-40° C./75% RH | 0.09 | 0.29 | 0.05 | ND | ND | 0.06 | ND | 0.12 | ND | ND | 0.61 | 101.9 |
| 3M-40° C./75% RH | 0.17 | 0.29 | 0.05 | ND | 0.01 | 0.06 | ND | 0.17 | ND | ND | 0.75 | 99.8 |

Formulation 15C:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | 0.04 | 0.28 | 0.06 | 0.02 | 0.02 | 0.07 | ND | 0.19 | ND | ND | 0.68 | 98.9 |
| 1M-25° C./60% RH | 0.03 | 0.28 | 0.05 | 0.03 | 0.04 | 0.05 | ND | 0.16 | ND | 0.01 | 0.66 | 103.1 |
| 2M-25° C./60% RH | 0.17 | 0.27 | 0.05 | ND | 0.02 | 0.06 | ND | 0.1 | ND | ND | 0.67 | 98.2 |
| 3M-25° C./60% RH | 0.05 | 0.24 | 0.04 | 0.03 | 0.02 | 0.05 | ND | 0.16 | ND | ND | 0.59 | 98.4 |
| 1M-30° C./65% RH | 0.04 | 0.28 | 0.05 | 0.02 | 0.03 | ND | ND | 0.16 | ND | ND | 0.59 | 103.6 |
| 2M-30° C./65% RH | 0.18 | 0.26 | 0.05 | ND | 0.02 | 0.05 | ND | 0.09 | ND | ND | 0.65 | 98.7 |
| 3M-30° C./65% RH | 0.07 | 0.22 | 0.04 | 0.02 | 0.02 | 0.06 | ND | 0.14 | ND | ND | 0.57 | 98.6 |
| 1M-40° C./75% RH | 0.09 | 0.28 | 0.05 | 0.03 | 0.02 | 0.12 | ND | 0.14 | ND | ND | 0.73 | 102.6 |
| 2M-40° C./75% RH | 0.28 | 0.27 | 0.04 | ND | 0.02 | 0.07 | ND | 0.09 | ND | ND | 0.77 | 98.8 |
| 3M-40° C./75% RH | 0.24 | 0.23 | 0.04 | 0.03 | 0.02 | 0.06 | ND | 0.11 | ND | 0.02 | 0.75 | 98.1 |

Formulation 15D:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | 0.06 | 0.05 | 0.05 | 0.04 | 0.04 | ND | ND | ND | ND | ND | 0.24 | 100.7 |
| 1M-25° C./60% RH | 0.05 | 0.04 | 0.02 | ND | 0.04 | 0.02 | ND | ND | ND | 0.01 | 0.19 | 103.4 |
| 2M-25° C./60% RH | 0.19 | 0.04 | 0.02 | ND | 0.04 | 0.03 | ND | ND | ND | 0.02 | 0.34 | 101.1 |
| 3M-25° C./60% RH | 0.08 | 0.02 | 0.02 | ND | 0.04 | ND | ND | ND | ND | 0.01 | 0.17 | 100.9 |
| 1M-30° C./65% RH | 0.06 | 0.04 | 0.02 | 0 | 0.05 | 0.02 | 0 | 0 | 0 | 0.01 | 0.21 | 103.3 |

-continued

| Condition | 21-Aldehyde | Desonide | Flunisolide Imp-A | Fluran-drenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| 2M-30° C./65% RH | 0.2 | 0.04 | 0.02 | ND | 0.04 | 0.03 | ND | ND | ND | ND | 0.33 | 100.6 |
| 3M-30° C./65% RH | 0.09 | 0.02 | 0.02 | ND | 0.04 | ND | ND | ND | ND | 0.01 | 0.17 | 101.4 |
| 1M-40° C./75% RH | 0.12 | 0.04 | 0.02 | 0 | 0.04 | 0.02 | 0 | 0 | 0 | 0.01 | 0.25 | 104.2 |
| 2M-40° C./75% RH | 0.31 | 0.04 | 0.02 | ND | 0.04 | 0.02 | ND | ND | ND | 0.02 | 0.45 | 101.7 |
| 3M-40° C./75% RH | 0.24 | 0.02 | 0.02 | ND | 0.04 | ND | ND | ND | ND | 0.02 | 0.34 | 101.3 |

Formulation 15E:

| Condition | 21-Aldehyde | Desonide | Flunisolide Imp-A | Fluran-drenolide | Flunisolide 11-Keto | Desonide 4 Fluoro | Delta 9,11 Analog | 9 Alpha Bromo | Flunisolide Acetate | Single max | Total Imp | Assay |
|---|---|---|---|---|---|---|---|---|---|---|---|---|
| Initial | ND | 0.24 | 0.04 | ND | ND | ND | ND | 0.18 | ND | 0.05 | 0.52 | 100.9 |
| 1M-25° C./60% RH | ND | 0.17 | ND | ND | ND | ND | ND | 0.18 | ND | ND | 0.35 | 97.8 |
| 2M-25° C./60% RH | 0.04 | 0.3 | 0.04 | 0.01 | 0.02 | 0.05 | nd | 0.21 | nd | ND | 0.67 | 100.3 |
| 3M-25° C./60% RH | 0.06 | 0.26 | 0.05 | 0.03 | 0.01 | 0.05 | ND | 0.18 | ND | ND | 0.64 | 98.4 |
| 1M-30° C./65% RH | 0.13 | 0.26 | 0.04 | ND | ND | 0.06 | ND | 0.13 | ND | ND | 0.62 | 97.5 |
| 2M-30° C./65% RH | 0.1 | 0.32 | 0.05 | ND | 0.02 | 0.06 | ND | 0.12 | ND | ND | 0.67 | 98.5 |
| 3M-30° C./65% RH | 0.11 | 0.31 | 0.05 | ND | 0.02 | 0.06 | ND | 0.18 | ND | ND | 0.73 | 95.2 |
| 1M-40° C./75% RH | 0.23 | 0.31 | ND | ND | ND | 0.21 | ND | 0.02 | ND | ND | 0.77 | 96.7 |
| 2M-40° C./75% RH | 0.24 | 0.31 | 0.05 | ND | 0.02 | 0.08 | ND | 0.09 | ND | 0.02 | 0.81 | 96.7 |
| 3M-40° C./75% RH | 0.34 | 0.3 | 0.04 | 0.02 | 0.02 | 0.07 | ND | 0.15 | ND | ND | 0.94 | 99.1 |

Manufacturing Procedure:

The components of the oil phase were taken in a stainless steel container and heated to a temperature between 65 to 70° C. The drug phase was prepared by dissolving flunisolide (either the anhydrous form or the hemihydrate form) in benzyl alcohol at 65° C., followed by sonication for 20 minutes. The oil phase was mixed with the drug phase.

The aqueous phase was prepared by mixing purified water, disodium edetate and glycerine in a stainless steel container and heating to a temperature between 65 to 70° C. Xanthan gum was dispersed in this solution under stirring.

The oil phase containing the drug phase was added to the aqueous phase under homogenization for 20 minutes to obtain an emulsion. Sepineo P 600 (as applicable) was added to the final emulsified bulk under homogenization for 10 minutes. The emulsion was cooled to room temperature (25° C.) under stirring.

Example 16: Topical Flunisolide Composition

According to other specific embodiments, topical flunisolide compositions for delivery of flunisolide to the site of a skin infection or other skin condition on the skin comprise those set forth in Table 16, which is set forth below:

TABLE 16

| Emulsion Components | Ingredients | (% w/w) |
|---|---|---|
| Drug + Oil Phase | Flunisolide Anhydrous | 0.25 |
| | Isopropyl alcohol | 5.0 |
| | Labrasol | 33.0 |
| | Transcutol P | 11.0 |
| | Sepineo P 600 | 4.0 |
| | Titanium dioxide + Aluminiumstarch octenylsuccinate (1:10) | 4.0 |
| Aqueous phase | Purified water | q.s. to 100 |

Stability Data for Table 16

| Condition | 21-Aldehyde | Desonide | Flunisolide Imp-A | Fluran-drenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | 0.03 | 0.31 | ND | 0.03 | 0.09 | ND | ND | 0.21 | ND | ND | 0.67 | 100.5 |
| 1M-25° C./60% RH | 0.05 | 0.28 | ND | ND | 0.24 | ND | ND | 0.19 | ND | 0.05 | 0.82 | 99.1 |
| 2M-25° C./60% RH | 0.00 | 0.20 | 0.03 | 0.03 | 0.39 | 0.06 | ND | 0.18 | ND | 0.24 | 1.3 | 97.7 |
| 3M-25° C./60% RH | 0.05 | 0.20 | ND | ND | 0.5 | 0.06 | ND | 0.12 | ND | 0.16 | 1.2 | 96.5 |
| 1M-30° C./65% RH | 0.07 | 0.23 | ND | ND | 0.18 | ND | ND | 0.17 | ND | 0.07 | 0.73 | 99.0 |
| 2M-30° C./65% RH | 0.02 | 0.2 | 0.03 | 0.03 | 0.38 | 0.06 | ND | 0.13 | ND | 0.27 | 1.28 | 98.5 |
| 3M-30° C./65% RH | 0.11 | 0.23 | 0.03 | ND | 0.51 | 0.06 | ND | 0.1 | ND | 0.33 | 1.5 | 95.3 |
| 1M-40° C./75% RH | 0.1 | 0.29 | ND | ND | 0.47 | ND | ND | 0.19 | ND | 0.25 | 1.32 | 95.5 |
| 2M-40° C./75% RH | 0.38 | 0.33 | 0.04 | 0.03 | 0.57 | 0.07 | ND | 0.07 | ND | 0.44 | 2.67 | 91.6 |
| 3M-40° C./75% RH | 0.49 | 0.40 | 0.03 | ND | 0.18 | 0.12 | ND | 0.05 | ND | 0.49 | 2.07 | 91.7 |

Manufacturing Procedure:

The components of oil phase were taken in a suitable container and stirred to mix. Flunisolide was added to the oil phase and the contents were mixed. The mixture was mixed with the required quantity of purified water with continuous stirring to form a clear microemulsion. Sepineo p 600 and Titanium dioxide-aluminiumstarch octenyl succinate were added to the microemulsion under homogenization for 5 minutes.

Example 17: Topical Flunisolide Composition

According to other specific embodiments, topical flunisolide compositions for delivery of flunisolide to the site of a skin infection or other skin condition on the skin comprise those set forth in Table 16, which is set forth below:

TABLE 17

| Emulsion | | Example Nos. | | |
|---|---|---|---|---|
| Components | Ingredients (% w/w) | 17A | 17B | 17C |
| Drug + Oil Phase | Flunisolide Hemihydrate | 0.25 | 0.25 | 0.25 |
| | Isopropyl myristate | 8 | 8 | 8 |
| | Polysorbate 80 | 13 | 13 | 13 |
| | Polysorbate 20 | 13 | 13 | 13 |
| | PEG 400 | 6.5 | 6.53 | 6.53 |
| | Glyceryl isostearate | — | 2 | 2 |
| | Sorbitan isostearate | — | 0.4 | 0.4 |
| | Sepineo P 600 | — | — | 4 |
| | Titanium dioxide - Aluminiumstarch octenylsuccinate (1:10) | — | — | 4 |
| Aqueous Phase | Purified water | q.s. to 100 | q.s. to 100 | q.s. to 100 |

Stability Data for Table 17

Formulation 17C:

| Condition | 21-Aldehyde | Desonide | Flunisolide Imp-A | Flurandrenolide | Flunisolide 11-Keto | Desonide 4 Fluoro | Delta 9,11 Analog | 9 Alpha Bromo | Flunisolide Acetate | Single max | Total Impurity | Assay (%) |
|---|---|---|---|---|---|---|---|---|---|---|---|---|
| Initial | 0.22 | 0.31 | 0.04 | 0.03 | 0.05 | ND | ND | 0.2 | ND | ND | 0.85 | 102.1 |
| 1M-25° C./60% RH | 0.08 | 0.19 | 0.05 | ND | ND | ND | ND | 0.18 | ND | 0.15 | 0.66 | 99.7 |
| 2M-25° C./60% RH | 0.11 | 0.27 | 0.04 | 0.03 | 0.06 | 0.05 | ND | 0.15 | ND | 0.21 | 0.95 | 99.9 |
| 3M-25° C./60% RH | 0.32 | 0.3 | 0.05 | ND | 0.07 | 0.06 | ND | 0.12 | ND | 0.28 | 1.23 | 97.2 |
| 1M-30° C./65% RH | 0.04 | 0.28 | 0.06 | ND | ND | ND | ND | 0.15 | ND | 0.19 | 0.73 | 100.8 |
| 2M-30° C./65% RH | 0.12 | 0.28 | 0.04 | 0.04 | 0.05 | 0.07 | ND | 0.14 | ND | 0.30 | 0.74 | 100.8 |
| 3M-30° C./65% RH | 0.67 | 0.31 | 0.05 | 0.03 | 0.11 | 0.09 | ND | 0.09 | ND | 0.55 | 1.98 | 96.7 |
| 1M-40° C./75% RH | 0.06 | 0.26 | 0.04 | 0.03 | 0.02 | ND | ND | 0.16 | ND | 0.19 | 0.76 | 98.6 |
| 2M-40° C./75% RH | 0.11 | 0.3 | 0.04 | 0.06 | 0.1 | 0.14 | ND | 0.05 | ND | 0.90 | 1.88 | 98.8 |
| 3M-40° C./75% RH | 0.40 | 0.33 | 0.04 | 0.01 | 0.09 | 0.18 | ND | 0.02 | ND | 0.70 | 1.88 | 95.7 |

Manufacturing Procedure:

The components of oil phase were taken in a suitable container and stirred to mix. Flunisolide was added to the oil phase and the content were mixed. The mixture was mixed with required quantity of purified water with continuous stirring to form clear microemulsion. Sepineo p 600 and Titanium dioxide-aluminiumstarch octenyl succinate were added to the microemulsion under homogenization for 5 minutes Although this application has been described in detail above, it will be understood by one of ordinary skill in the art that various modifications can be made without departing from the spirit of the invention. The use of the phrase "means for" or "step for" in the claims indicates an intention to invoke 35 U.S.C. § 112, 6$^{th}$ paragraph. However, unless the term "means" or "step" are specifically recited in a claim, 35 U.S.C. § 112, 6$^{th}$ paragraph is not intended to be invoked.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

What is claimed is:

1. A stable topical flunisolide composition for treating a skin condition comprising: a therapeutically effective amount of flunisolide or a salt thereof; and a solubilizing agent that solubilizes the flunisolide, wherein the solubilizing agent is benzyl alcohol, which is used in an amount of about 2.0-4.0% w/w, wherein about 90% to about 99% of the flunisolide is in solubilized form and optionally comprising antioxidant and wherein said composition is an emulsion in the form of a cream, gel, oil, ointment, paste, or lotion which is chemically and physically stable upon storage.

2. The stable topical flunisolide composition of claim 1, further comprising an emulsifying agent.

3. The stable topical flunisolide composition of claim 2, wherein the emulsifying agent is selected from the group consisting of polyoxyl 40 hydrogenated castor oil, vegetable oil hydrogenated, lecithin, steareth 2, glyceryl monostearate, glyceryl stearate/PEG 100 stearate, polyoxyl 20 cetostearyl ether, steareth-21, polysorbate 60, PPG 15 stearyl ether, sorbitan monostearate, sodium lauryl sulfate, polyethylene glycol monopalmitostearate, cetostearyl alcohol, cetyl alcohol, stearyl alcohol, cetyl esters wax, white petrolatum, polysorbate 20, polysorbate 80, caprylocaproyl polyoxyl-8 glycerides, and mixtures thereof.

4. The stable topical flunisolide composition of claim 1, further comprising an emollient.

5. The stable topical flunisolide composition of claim 4, wherein the emollient is selected from the group consisting of mineral oil, lanolin alcohol, octyldodecanol, oleyl alcohol, isosteric acid, oleic acid, isopropyl myristate, medium-chain triglycerides, olive oil, soybean oil, isopropyl palmitate, iosopropyl isostearate, propylene glycol dicaprylate, cocoyl caprylocarprate and combinations thereof.

6. The stable topical flunisolide composition of claim 1, further comprising a humectant.

7. The stable topical flunisolide composition of claim 6, wherein the humectant is selected from glycerin, alkoxylated methyl glucose derivatives, isopropyl isostearate and combinations thereof.

8. The stable topical flunisolide composition of claim 1, further comprising a moisturizer.

9. The stable topical flunisolide composition of claim 8, wherein the moisturizer is selected from dimethicone 350, dimethicone 360, cyclomethicone, and combinations thereof.

10. The stable topical flunisolide composition of claim 1, further comprising a preservative.

11. The stable topical flunisolide composition of claim 10, wherein the preservative is selected from methyl paraben, propyl paraben, diazodinyl urea and combinations thereof.

12. The stable topical flunisolide composition of claim 1, further comprising a thickening agent.

13. The stable topical flunisolide composition of claim 12, wherein the thickening agent is selected from acrylate co-polymers, carbomer homopolymer Type C, and mixtures thereof and combinations thereof.

14. The stable topical flunisolide composition of claim 1, further comprising an anti-oxidant.

15. The stable topical flunisolide composition of claim 14, wherein the anti-oxidant is butylatedhydroxytoluene (BHT).

16. The stable topical flunisolide composition of claim 1, further comprising a chelating agent.

17. The stable topical flunisolide composition of claim 16, wherein the chelating agent is disodium edetate.

18. The stable topical flunisolide composition of claim 1, further comprising one or more of the following: an emulsifying agent, an emollient, a preservative, a chelating agent, an anti-oxidant, a thickener, a humectant, a moisturizer, an opacifier, a pH modifier and combinations thereof.

19. The stable topical flunisolide composition of claim 1, wherein the composition is an emulsion in the form of a cream.

20. The stable topical flunisolide composition of claim 1, wherein the amount of flunisolide present is between about 0.01% to about 0.35% by weight of the composition.

21. The stable topical flunisolide composition of claim 1, wherein about 97% to about 99% of the flunisolide is solubilized.

22. A method for treating a skin condition in a subject comprising administering to a subject in need thereof a topical flunisolide composition according to claim 1.

23. The method of claim 22, wherein the topical composition is placed directly at the site of the skin condition.

24. The method of claim 22, wherein the topical composition does not result in substantial systemic exposure of flunisolide.

25. The method of claim 22, wherein the flunisolide is substantially solubilized.

26. The method of claim 25, wherein the solubilized flunisolide is in a microemulsion or a nanoemulsion.

27. The method of claim 26, wherein the topical composition is a cream.

28. The method of claim 22, wherein the amount of flunisolide present in the topical composition is between about 0.01% to about 0.35% by weight of the composition.

29. The method of claim 22, wherein the amount of flunisolide present in the topical composition is about 0.25% by weight of the composition.

30. The method of claim 22, wherein the amount of flunisolide present in the topical composition is about 0.1% by weight of the composition.

31. The method of claim 22, wherein the skin condition is dermatosis, pruritis, psoriasis, seborrhea, contact dermatitis, rosacea, atopic dermatitis, an inflammation of the skin, or a combination thereof.

32. The method of claim 31, wherein the skin condition is psoriasis, atopic dermatitis or inflammation of the skin.

33. The method of claim 22, wherein the topical composition is formulated for administration to skin or scalp.

34. A stable topical flunisolide composition for treating a skin condition comprising: a therapeutically effective amount of flunisolide or a salt thereof; and a solubilizing agent that solubilizes the flunisolide, wherein the solubilizing agent is benzyl alcohol which is used in an amount of about 2.0-4.0% w/w, wherein about 90% to about 99% of the flunisolide is in solubilized form and optionally comprising antioxidant, and wherein the flunisolide or salt thereof is in amount of about 0.1% w/w to about 0.25% w/w based on the total weight of the topical flunisolide composition wherein said composition is an emulsion in the form of a cream, gel, oil, ointment, paste, or lotion which is physically and chemically stable.

35. The stable topical flunisolide composition of claim 34, wherein the amount of flunisolide or flunisolide related impurities in the composition is no more than about 10% after 6 month storage at 40° C. and 75% humidity.

* * * * *